(12) United States Patent
Hotta

(10) Patent No.: US 9,329,025 B2
(45) Date of Patent: May 3, 2016

(54) MEASURING DEVICE

(71) Applicant: FUJI XEROX CO., LTD., Tokyo (JP)

(72) Inventor: Hiroyuki Hotta, Kanagawa (JP)

(73) Assignee: FUJI XEROX CO., LTD., Tokyo (JP)

( * ) Notice: Subject to any disclaimer, the term of this patent is extended or adjusted under 35 U.S.C. 154(b) by 68 days.

(21) Appl. No.: 14/202,768

(22) Filed: Mar. 10, 2014

(65) Prior Publication Data

US 2014/0355006 A1    Dec. 4, 2014

(30) Foreign Application Priority Data

May 28, 2013    (JP) ................................ 2013-111891

(51) Int. Cl.
| | | |
|---|---|---|
| G01N 21/47 | (2006.01) | |
| G01N 21/41 | (2006.01) | |
| G01B 9/02 | (2006.01) | |
| G01B 11/06 | (2006.01) | |
| G01N 21/01 | (2006.01) | |

(52) U.S. Cl.
CPC ............ *G01B 11/0608* (2013.01); *G01N 21/47* (2013.01); *G01B 9/02015* (2013.01); *G01N 21/41* (2013.01); *G01N 2021/0106* (2013.01)

(58) Field of Classification Search
CPC .................................................. G01B 11/0608
See application file for complete search history.

(56) References Cited

U.S. PATENT DOCUMENTS

| | | | | |
|---|---|---|---|---|
| 3,582,769 A | * | 6/1971 | Brandenburg ............ | G01F 5/12 324/207.22 |
| 3,619,059 A | * | 11/1971 | Muller ..................... | G01J 5/60 250/226 |
| 3,967,114 A | * | 6/1976 | Cornillault ............. | G01B 11/02 250/236 |
| 4,103,309 A | * | 7/1978 | Massa ..................... | G02B 7/40 352/140 |
| 4,299,491 A | * | 11/1981 | Waters ................... | G01B 11/24 356/3.05 |
| 4,489,239 A | * | 12/1984 | Grant ..................... | G01N 21/39 250/338.5 |
| 4,639,140 A | * | 1/1987 | Lerat ..................... | B23K 9/1274 356/4.06 |
| 4,770,532 A | * | 9/1988 | Ito ........................ | G01B 11/0608 356/625 |
| 5,054,912 A | * | 10/1991 | Kuchel .................. | G01S 17/87 355/487 |
| 5,056,913 A | * | 10/1991 | Tanaka ................... | G01S 7/499 250/225 |
| 5,104,225 A | * | 4/1992 | Masreliez ................ | G01D 5/38 250/237 G |
| 5,644,141 A | * | 7/1997 | Hooker .................. | G01B 11/24 250/205 |
| 5,870,199 A | * | 2/1999 | Wurbs .................... | G01B 11/24 250/559.23 |
| 6,094,270 A | * | 7/2000 | Uomori .................. | G01S 17/46 356/623 |
| 7,310,140 B2 | * | 12/2007 | Eom ...................... | G01N 21/9501 356/237.2 |
| 7,616,303 B2 | * | 11/2009 | Yang ..................... | A61B 5/14535 356/300 |
| 7,684,053 B2 | * | 3/2010 | Chow .................... | G01B 11/026 356/602 |
| 2003/0052255 A1 | | 3/2003 | Hotta | |

FOREIGN PATENT DOCUMENTS

| | | |
|---|---|---|
| JP | A-6-213623 | 8/1994 |
| JP | A-6-213658 | 8/1994 |
| JP | A-6-254748 | 9/1994 |
| JP | A-2008-46079 | 2/2008 |
| JP | B2-4123878 | 7/2008 |

* cited by examiner

*Primary Examiner* — Tri Ton
*Assistant Examiner* — Jarreas C Underwood
(74) *Attorney, Agent, or Firm* — Oliff PLC

(57) ABSTRACT

Provided is a measuring device including a photoelectric conversion unit that receives a light beam emitted from a position measurement object by different optical path lengths and that outputs an electrical signal corresponding to intensity of the received light beam for each optical path length, and a measuring unit that measures a position of the position measurement object based on a ratio of two electrical signals out of the electrical signals by optical path lengths acquired from the photoelectric conversion unit.

13 Claims, 34 Drawing Sheets

FIG. 17
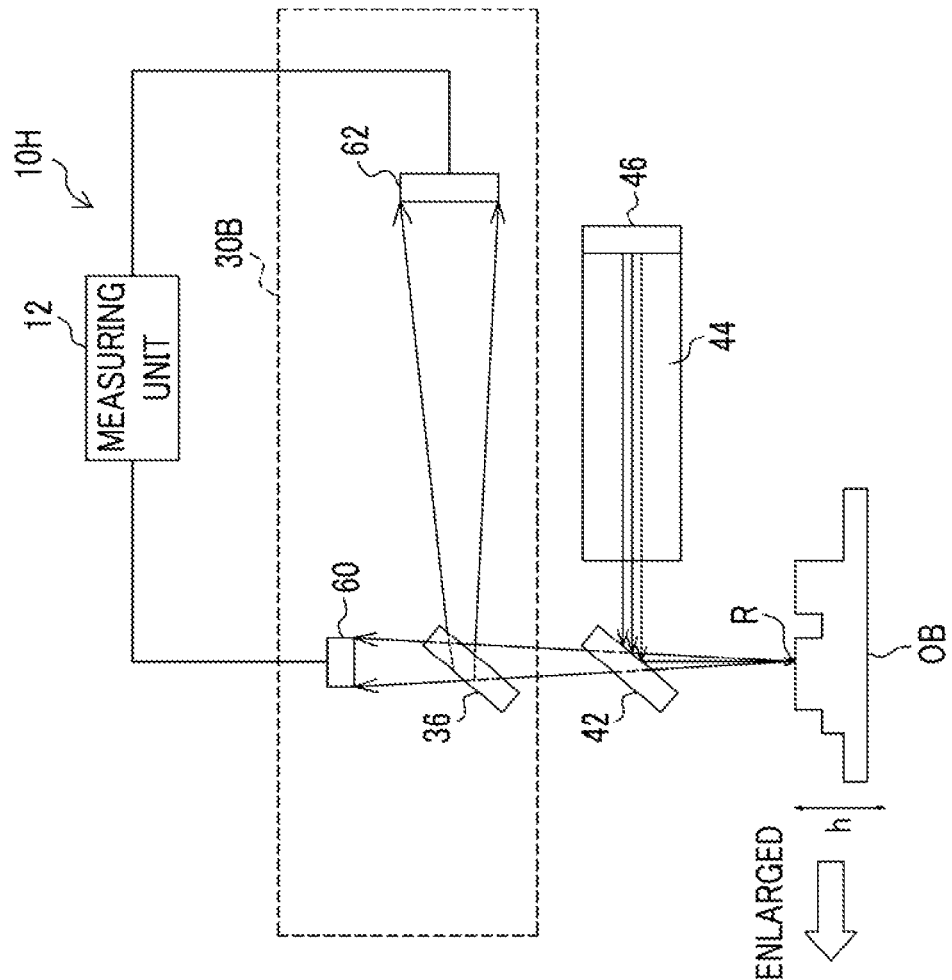
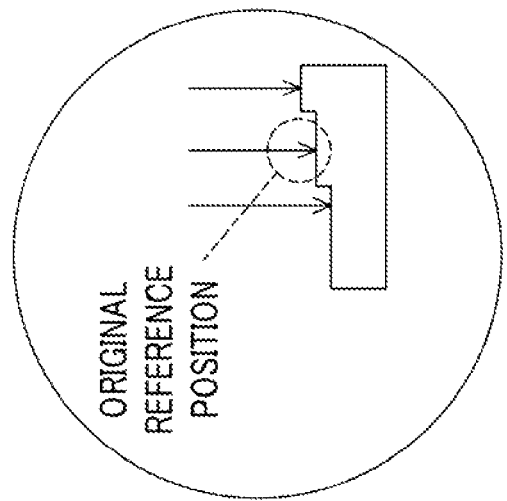

EXAMPLE WHERE VARIATION RANGE OF
EMISSION POINT OR REFLECTION POINT
OR CONDENSATION POINT RISES

EXAMPLE WHERE VARIATION RANGE OF
EMISSION POINT OR REFLECTION POINT
OR CONDENSATION POINT RISES

EMISSION POINT OR
REFLECTION POINT OR
CONDENSATION POINT

MEASURING DEVICE

CROSS-REFERENCE TO RELATED APPLICATIONS

This application is based on and claims priority under 35 USC 119 from Japanese Patent Application No. 2013-111891 filed May 28, 2013.

BACKGROUND

Technical Field

The present invention relates to a measuring device.

SUMMARY

According to an aspect of the invention, there is provided a measuring device including:

a photoelectric conversion unit that, receives a light beam emitted from a position measurement object by different optical path lengths and that outputs an electrical signal corresponding to intensity of the received light beam for each optical path length; and a measuring unit that measures a position of the position measurement object based on a ratio of two electrical signals out of the electrical signals by optical path lengths acquired from the photoelectric conversion unit.

BRIEF DESCRIPTION OF THE DRAWINGS

Exemplary embodiments of the present invention will be described in detail based on the following figures, wherein:

FIG. 17 is a diagram illustrating another example of the configuration of the measuring device according to the third exemplary embodiment;

DETAILED DESCRIPTION

Hereinafter, exemplary embodiments of the present invention will be described with reference to the accompanying drawings.

First Exemplary Embodiment

Figure 1:
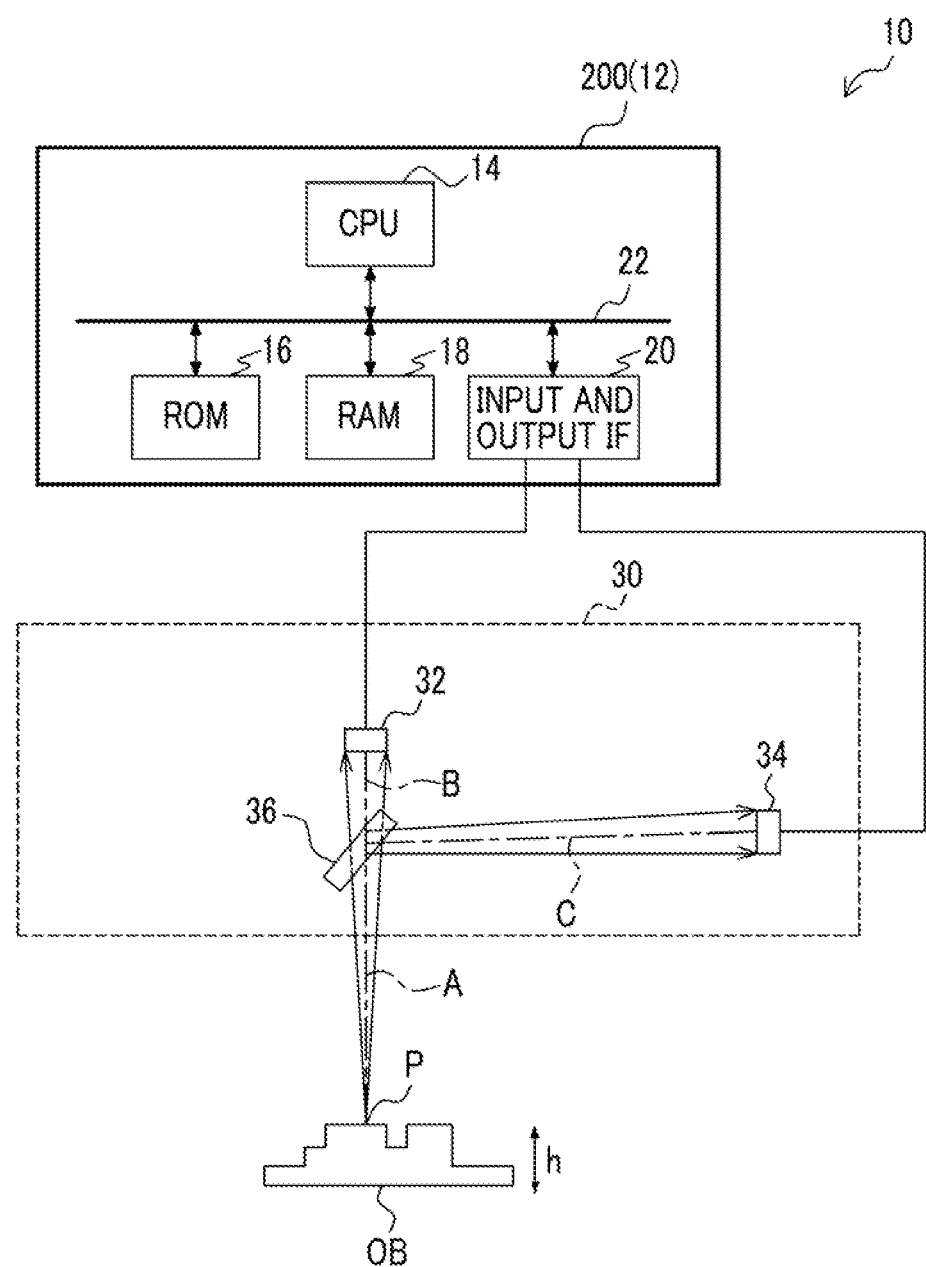
FIG. 1, is a diagram illustrating an example of a configuration of a measuring device according to a first exemplary embodiment.

FIG. 1 is a diagram illustrating an example of a configuration of a measuring device 10 according to this exemplary embodiment. The measuring device 10 measures a position h in a height direction of a measurement object OB. Here, the height direction means a direction indicated by an arrow in FIG. 1. In this exemplary embodiment, the measurement object OB includes a light source and a light beam emitted from the light source is emitted from an emission point P of the measurement object OB. In the first exemplary embodiment, a measurement portion (emission point P herein) of the measurement object OB is considered as a position measurement target (hereinafter, simply referred to as a measurement target) of the measuring device 10.

The measuring device 10 includes a measuring unit 12 and a photoelectric conversion unit 30. The photoelectric conversion unit 30 is disposed at a position at which a light beam (emitted light) emitted from the emission point P of the measurement object OB may be received. The emission point P emits a diffused light beam having a spread angle.

The light source of the measurement object OB may be formed of an LED so as to emit a light beam of the LED from the emission point P. The light source of the measurement object OB may be formed of a semiconductor laser so as to emit a laser beam from the emission point P. Specifically, a surface emitting laser (SEL) that emits a light beam in a direction perpendicular to a semiconductor substrate, more specifically, a vertical cavity surface emitting laser (VCSEL) in which a resonator is formed to be perpendicular to a semiconductor substrate, may be used as the semiconductor laser. For example, the semiconductor laser may be an edge emitting laser (EEL) in which a resonator is formed in a direction parallel to a semiconductor substrate and that emits a light beam in the direction parallel to the semiconductor substrate from a cleaved side surface.

The photoelectric conversion unit 30 is configured to receive a light beam emitted from the emission point P with different optical path lengths and outputs an electrical signal corresponding to received light intensity by the optical path lengths.

The photoelectric conversion unit 30 includes a first photoelectric conversion surface 32, a second photoelectric conversion surface 34, and a half mirror 36. The first photoelectric conversion surface 32 is disposed in an emission direction of a light beam from the emission point P and the half mirror 36 is disposed between the first photoelectric conversion surface 32 and the emission point P. The light beam emitted from the emission point P is incident on the half mirror 36. The half mirror 36 transmits and reflects an incident light beam. The ratio of transmission and reflection of the half mirror 36 is 1:1. The first photoelectric conversion surface 32 is disposed in the emission direction of a transmitted light beam of the half mirror 36 and the second photoelectric conversion surface 34 is disposed in the emission direction of a reflected light beam. The first photoelectric conversion surface 32 and the second photoelectric conversion surface 34 receive a light beam from the emission point P which is incident via the half mirror 36, photo-electrically convert the received light beam, and outputs an electrical signal corresponding to the received light intensity.

An imaging device such as a charge coupled device (CCD) or a complementary metal oxide semiconductor (CMOS) may be used as the first photoelectric conversion surface 32 and the second photoelectric conversion surface 34. Here, it is assumed that a photodiode (PD) is used. A photodiode outputs an electrical signal corresponding to the received light intensity. The larger the received light intensity becomes, the higher the output value of the photodiode becomes. The time required for a photoelectric conversion in a photodiode is shorter than those in the imaging device such as a CCD. This is because correction of ambient light performed when an imaging device is used is not necessary for the photodiode and thus much time is not required for signal processing. The cost is lower than that of a high-performance imaging device capable of performing a fast process. In this exemplary embodiment, the first photoelectric conversion surface 32 is formed of a one photodiode and the second photoelectric conversion surface 34 is formed of one photodiode.

The optical path length from the emission point P to the first photoelectric conversion surface 32 is expressed by A+B, and the optical path length from the emission point P to the second photoelectric conversion surface 34 is expressed by A+C. Here, A represents the optical path length from the emission point P to the half mirror 36, B represents the optical path length from the half mirror 36 to the first photoelectric conversion surface 32, and C represents the optical, path length from the half mirror 36 to the second photoelectric conversion surface 34. The first photoelectric conversion surface 32 and the second photoelectric conversion surface 34 are disposed so that the optical path length B is shorter than the optical path length C (that is, B<C).

The optical path of the light beam emitted from the measurement target is bent by the half mirror 36, but when it is assumed that the first photoelectric conversion surface 32 and the second photoelectric conversion surface 34 are virtually arranged in a straight form and a light beam is incident on the first photoelectric conversion surface 32 and the second photoelectric conversion surface 34 as a straight beam with the optical path not bent, the light-receiving surfaces of the first photoelectric conversion surface 32 and the second photoelectric conversion surface 34 form an angle perpendicular to or substantially perpendicular to the central axis of the light beam emitted from the measurement target (the angles of the light-receiving surfaces of the first photoelectric conversion surface 32 and the second photoelectric conversion surface 34 about the optical path are substantially the same).

In a photoelectric conversion unit 30A and a photoelectric conversion unit 30B to be described later in a second exemplary embodiment and a third exemplary embodiment or in various modification examples, the angles of the light-receiving surfaces of the plural photoelectric conversion surfaces about the optical path are the same or substantially the same.

The measuring unit 12 measures a position h in the height direction of the emission point P based on the ratio of two electrical signals (hereinafter, referred to as an output ratio) of the electrical signals by optical path lengths acquired by the photoelectric conversion unit 30. In this exemplary embodiment, since the number of photoelectric conversion surfaces of the photoelectric conversion unit 30 is two, the measuring unit 12 calculates the output ratio of the two photoelectric conversion surfaces and measures the position h based on the output ratio.

As described above, in this exemplary embodiment, two electrical signals having different optical path lengths are acquired by the first photoelectric conversion surface 32 and the second photoelectric conversion surface 34. The measuring unit 12 acquires the two electrical signals, calculates the output ratio, and measures the position h in the height direction of the emission point P.

As illustrated in FIG. 1, the measuring unit 12 may be embodied by a computer 200. The computer 200 includes a central processing unit (CPU) 14, a read only memory (ROM) 16, a random access memory (RAM) 18, and an input and output interface (input and output IF) 20, which are connected via a bus 22.

The ROM 16 mainly stores various programs executed by the CPU 14 or a variety of data thereof or the like in advance. Various programs include a program for acquiring output values of the first photoelectric conversion surface 32 and the second photoelectric conversion surface 34 of the photoelectric conversion unit 30 and measuring the position of the emission point P. The ROM 16 stores a table in which the position h in the height direction is correlated with the output ratio V1/V2 or a relational expression of the position h in the height direction and the output ratio V1/V2, as will be described later. The RAM 18 temporarily stores a variety of data based on the processes of the CPU 14 or the like.

A recording medium storing the programs executed by the CPU 14 is not limited to the ROM 16, and may be a hard disk drive (HDD), a CD-ROM, a portable recording medium such as a DVD disk, a magneto-optical disk, and an IC card, a storage device such as an HDD disposed outside the measuring unit 12, a database connected via a network, another computer system, or a database thereof.

The input and output IF 20 is connected to the first photoelectric conversion surface 32 and the second photoelectric conversion surface 34. The input and output IF 20 outputs the electrical signals output from the first photoelectric conversion surface 32 and the second photoelectric conversion surface 34 to the CPU 14. A signal processing circuit such as an amplifier amplifying the electrical signals output from the first photoelectric conversion surface 32 and the second photoelectric conversion surface 34 may be disposed between the input and output IF 20 and the first photoelectric conversion surface 32 and the second photoelectric conversion surface 34.

The principle of measuring a position according to this exemplary embodiment will be described below in brief.

In this exemplary embodiment, the position h in the height direction of the emission point P of the measurement object OB is measured based on the ratio of the outputs of the first photoelectric conversion surface 32 and the second photoelectric conversion surface 34 having different optical path lengths from the emission point P to the light-receiving surface.

Figure 2:
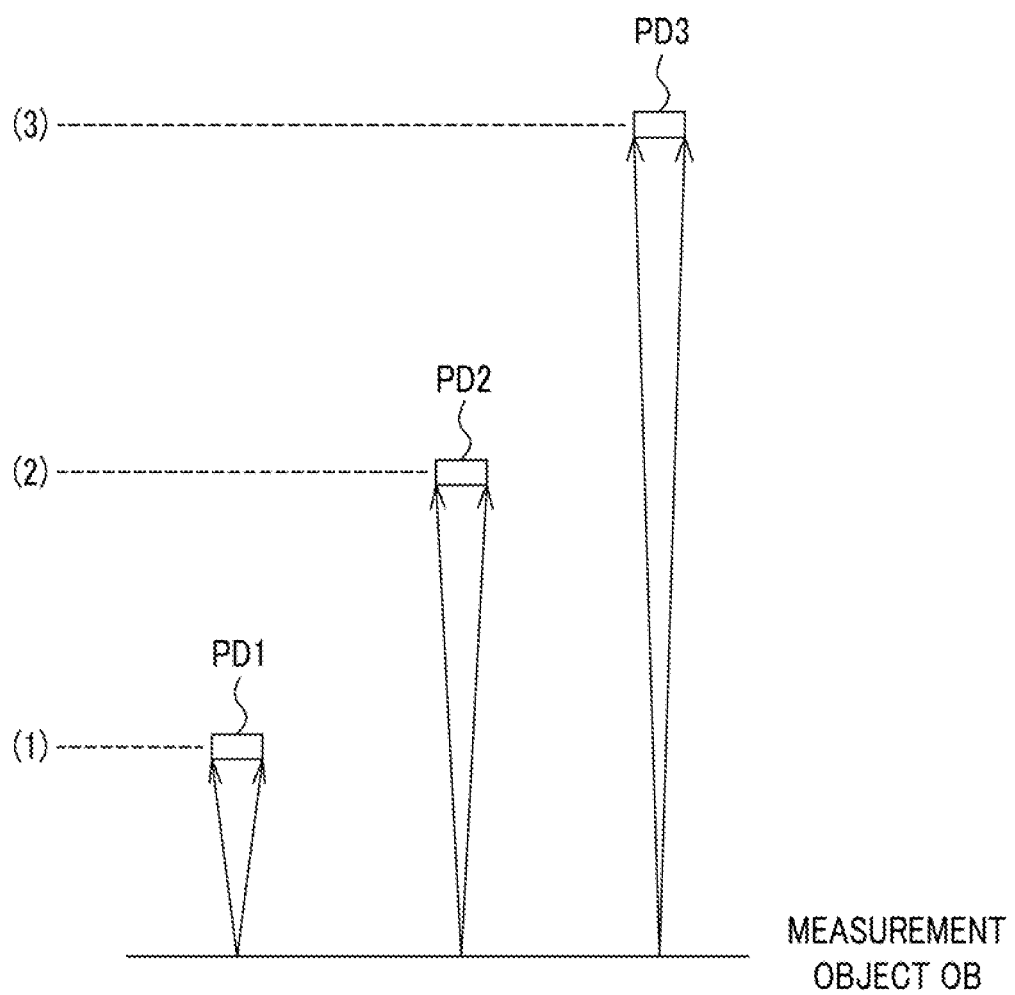
FIG. 2 is a diagram schematically illustrating receiving states of light emitted from a measurement object on photoelectric conversion surfaces when the photoelectric conversion surfaces having the same area are arranged to have different distances (optical path lengths) from the measurement object.
Figure 3:
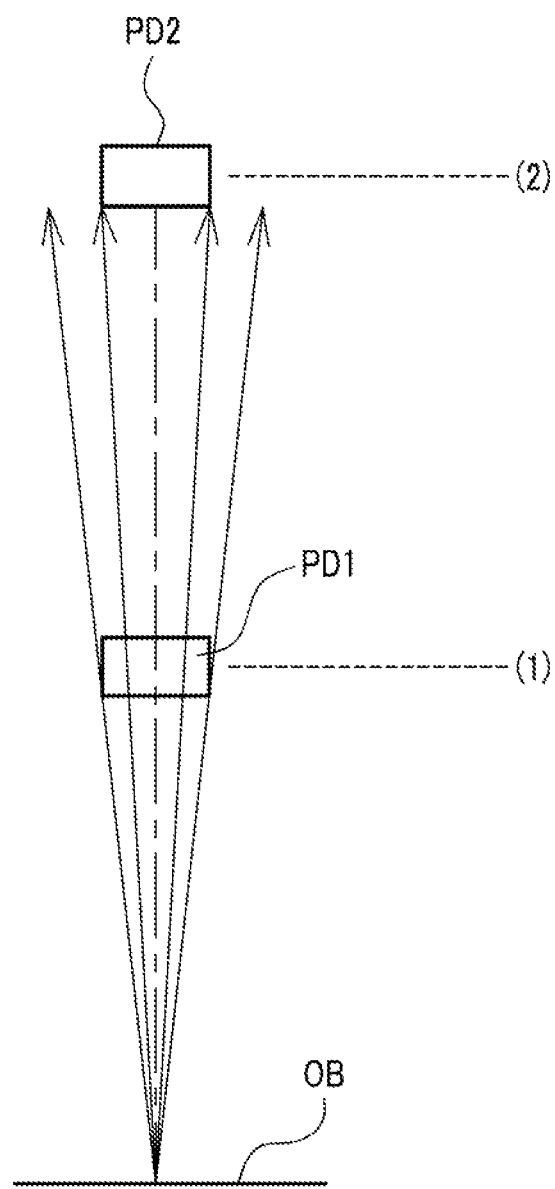
FIG. 3 is a diagram illustrating optical, axes of light incident on the photoelectric conversion surfaces illustrated in FIG. 2 in an overlapping manner.

FIG. 2 is a diagram schematically illustrating receiving states of a light beam emitted from the measurement object OB in photoelectric conversion surfaces PD1, PD2, and PD3 when the photoelectric conversion surfaces PD1, PD2, and PD3 having the same area are arranged to have different distances (optical path lengths) from the measurement object OB. The distances from the emission point of a light beam of the measurement object OB to (1) to (3) are the optical path lengths of the photoelectric conversion surfaces PD1, PD2, and PD3. FIG. 3 is a diagram illustrating optical axes of light incident on the photoelectric conversion surfaces PD1 and PD2 illustrated in FIG. 2 in an overlapping manner. As illustrated in FIGS. 2 and 3, since the photoelectric conversion surface having a shorter distance (shorter optical path length) from the measurement object OB receives an incident light beam having a larger spread angle than the photoelectric conversion surface having a longer distance (longer optical path length) from the measurement object OB, the output becomes higher.

In an actual configuration, in order to measure a distance from one point (emission point P in this exemplary embodiment) of the measurement object OB, it is necessary to arrange plural photoelectric conversion surfaces so as to receive a light beam emitted from the same point. Therefore, in this exemplary embodiment, the photoelectric conversion unit 30 is configured to make the optical path lengths different using the half mirror 36 and to receive the emitted light beam from the emission point P of the measurement object OB using the first photoelectric conversion surface 32 and the second photoelectric conversion surface 34 as a set, as illustrated in FIG. 1.

In FIG. 1, comparing the output values of the first photoelectric conversion surface 32 and the second photoelectric conversion surface 34, the increasing ratio of the output value of the first photoelectric conversion surface 32 is greater than that of the output value of the second photoelectric conversion surface 34. By using this point, it is possible to calculate the distance (the position h in the height direction) from the output ratio of the first photoelectric conversion surface 32 and the second photoelectric conversion surface 34.

Figure 4:
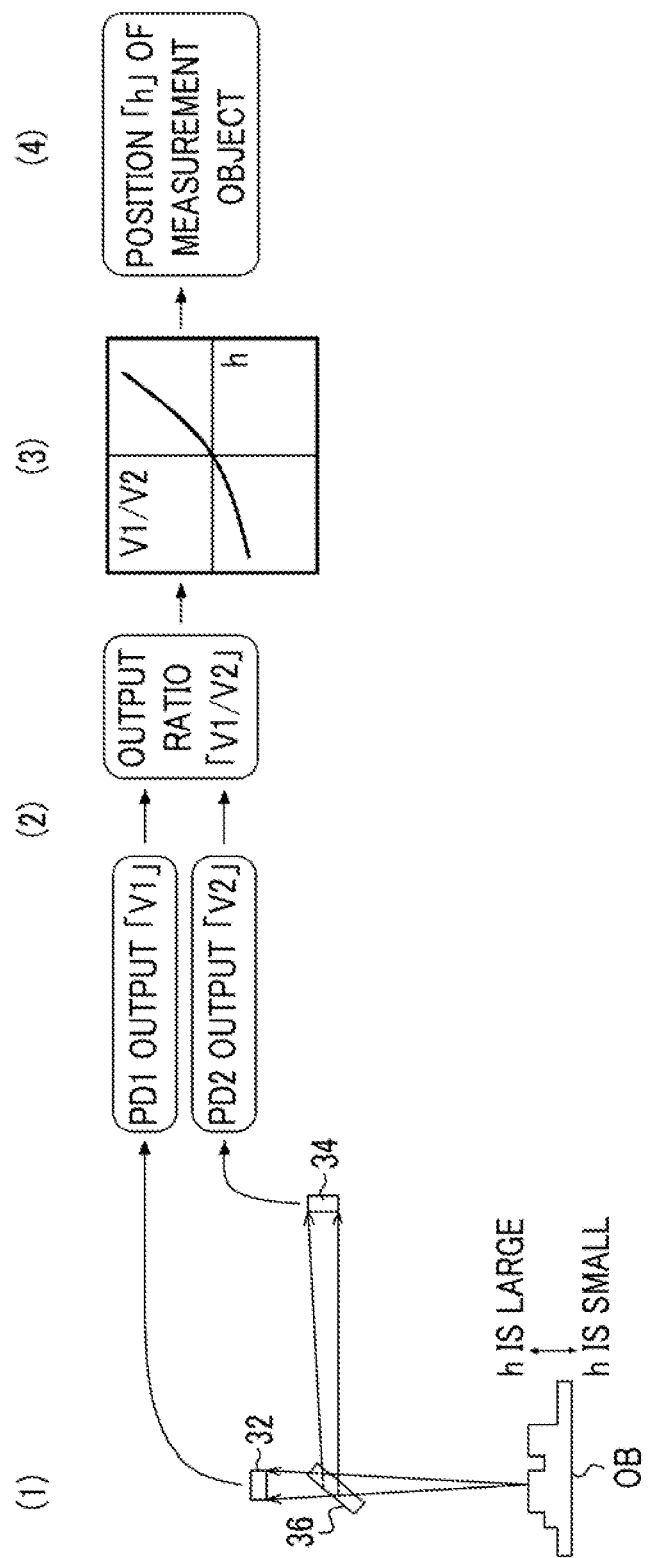
FIG. 4 is a diagram illustrating a measuring process in a measuring unit.

Regarding the sequence of calculating the output values, as illustrated in FIG. 4, in a measuring system in which the position h in the height direction from the measurement object OB may be changed in advance, the output values of the first photoelectric conversion surface 32 and the second photoelectric conversion surface 34 are acquired while changing the position h in the height direction of the measurement object OB (see (1) of FIG. 4), and the output ratio thereof is calculated ((2) of FIG. 4). Here, the output value of the first photoelectric conversion surface 32 is defined as V1, the output value of the second photoelectric conversion surface 34 is defined as V2, and the output ratio of the first photoelectric conversion surface 32 and the second photoelectric conversion surface 34 is defined as V1/V2.

In this way, the table in which the position h in the height direction is correlated with the output ratio V1/V2 or the relational expression (approximate expression for calculating the position h from the output ratio V1/V2) of the position h in the height direction and the output ratio V1/V2 is prepared in advance (see (3) of FIG. 4), and the position h is calculated with reference to the table or the approximate expression based on the output ratio in actual measurement (see (4) of FIG. 4). In (3) of FIG. 4, the vertical axis represents the output ratio V1/V2 and the horizontal axis represents the position h. V2/V1 instead of V1/V2 may be used as the output ratio.

The table or the approximate expression is stored in advance in the ROM 16.

Figure 5:
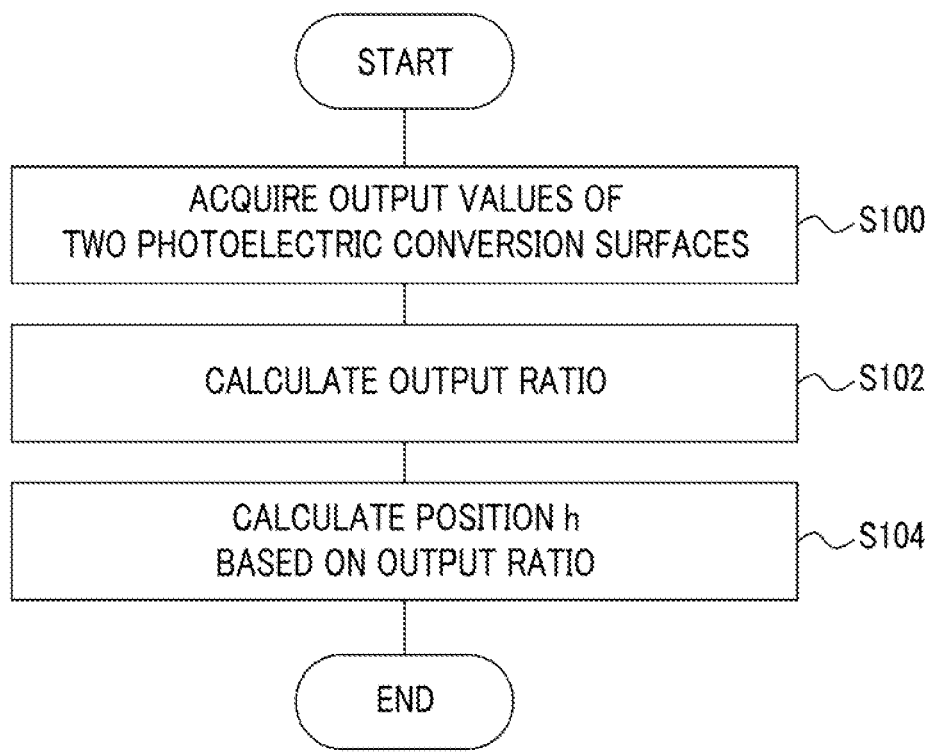
FIG. 5 is a flowchart illustrating the flow of the measuring process in the measuring unit.

FIG. 5 is a flowchart illustrating the flow of the measuring process in the measuring unit 12, which is embodied by causing the CPU 14 to execute the program.

In step 100, the CPU 14 acquires the output values V1 and V2 of the first photoelectric conversion surface 32 and the second photoelectric conversion surface 34.

In step 102, the CPU 14 calculates the output ratio V1/V2 from the output values V1 and V2 of the first photoelectric conversion surface 32 and the second photoelectric conversion surface 34.

In step 104, the CPU 14 calculates the position h from the output ratio V1/V2 using the table or the approximate expression stored in the ROM 16.

The number of photoelectric conversion surfaces in the photoelectric conversion unit 30 may be two or three or more. When three or more photoelectric conversion surfaces are provided, two photoelectric conversion surfaces are selected, the output ratio thereof is calculated, and then the position h is calculated. Here, when the number of photoelectric conversion surfaces increases, the number of half mirrors also increases and thus light intensity decreases. Accordingly, it is preferable that the number of photoelectric conversion surfaces be as small as possible. Two or more sets of two photoelectric conversion surfaces for calculating the output ratio may be provided. Accordingly, it is possible to measure or cancel characteristics depending on the difference in emission direction.

The light-receiving areas of the first photoelectric conversion surface 32 and the second photoelectric conversion surface 34 may be equal to or different from each other. An exemplary embodiment in which the light-receiving areas are different from each other will also be described in a "third exemplary embodiment" and "various modification examples".

Second Exemplary Embodiment

In the first exemplary embodiment, a light beam emitted from the emission point P of the measurement object OB is received by the photoelectric conversion unit 30 and the position h of the emission point P is calculated. In a second exemplary embodiment, a measurement object Ob is irradiated with a light beam from a light source, a reflected light beam from the measurement object OB is received, and the position h of a measurement part of the measurement object OB, that is, the position h of a reflection point R which is the emission position of the reflected light beam. Therefore, since the measurement target in the second exemplary embodiment is the reflection point R, the emission point P emitting a light beam may not be disposed in the measurement object OB in this exemplary embodiment.

In this exemplary embodiment, elements identical or equivalent to those of the measuring device 10 according to the first exemplary embodiment are referenced by the same reference signs and description thereof will not be repeated.

Figure 6:
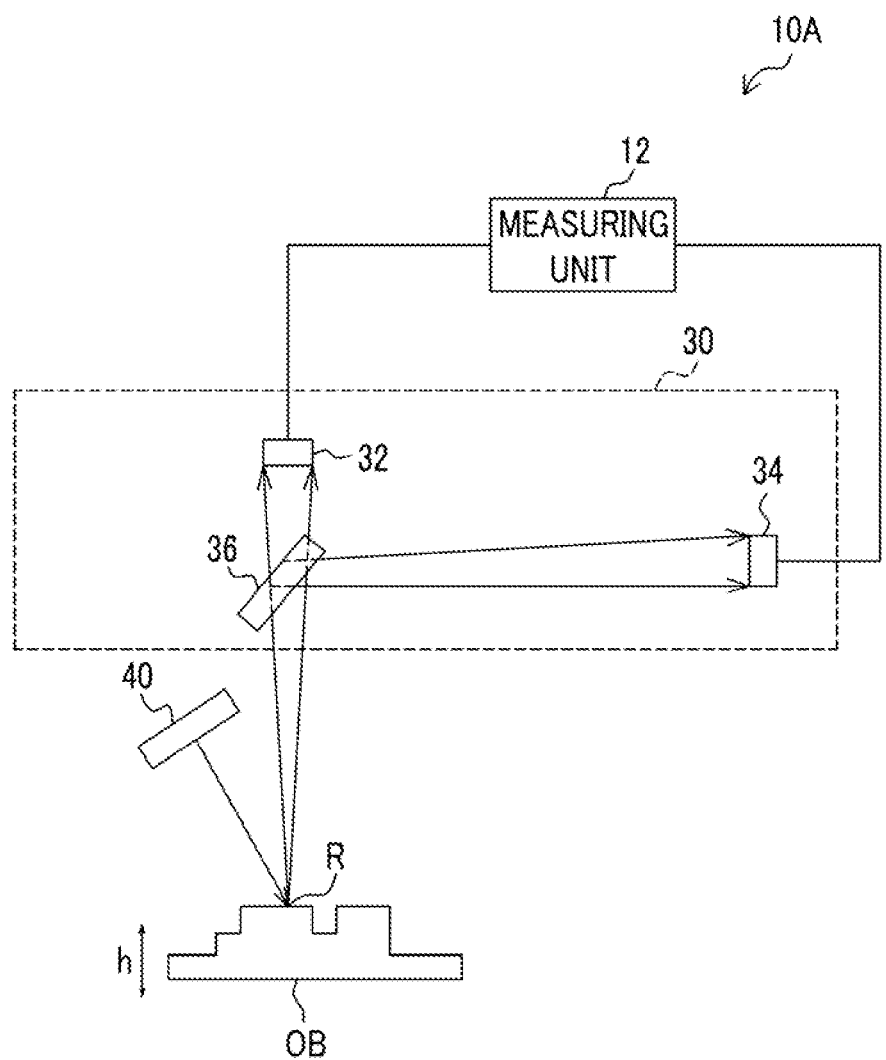
FIG. 6 is a diagram illustrating an example of a configuration of a measuring device according to a second exemplary embodiment.

FIG. 6 is a diagram illustrating an example of a configuration of a measuring device according to the second exemplary embodiment. A measuring device 10A according to this exemplary embodiment includes the measuring unit 12, the photoelectric conversion unit 30, and a light source 40. The measuring unit 12 and the photoelectric conversion unit 30 have the same configurations as in the first exemplary embodiment. The arrangement of the first photoelectric conversion surface 32, the second photoelectric conversion surface 34, and the half mirror 36 in the photoelectric conversion unit 30 is the same as in the first exemplary embodiment.

As illustrated in FIG. 6, the photoelectric conversion unit 30 is disposed to receive a reflected light beam reflected from the surface (irradiation position with a light beam) of the measurement object OB in a direction (a substantially normal direction) substantially perpendicular to the surface.

The light source 40 is disposed to irradiate the surface (irradiation position with a light beam) of the measurement object OB with a light beam from a direction inclined about the surface. Accordingly, the measurement object OB is irradiated with a light beam at an incidence angle of a predetermined magnitude or more. The light source 40 may include a semiconductor laser or an LED. Specifically, a surface emitting laser (SEL) may be used as the semiconductor laser. More specifically, a vertical cavity surface emitting laser (VCSEL) may be used. The semiconductor laser may be, for example, an edge emitting laser (EEL).

The measurement object OB is irradiated with a light beam from the light source 40, and the reflected light beam (diffused reflected light beam) is received by the first photoelectric conversion surface 32 and the second photoelectric conversion surface 34 via the half mirror 36. The first photoelectric conversion surface 32 and the second photoelectric conversion surface 34 are disposed to have different optical path lengths until the light beam emitted (reflected) from the measurement object OB is received, similarly to the first exemplary embodiment, and the measuring unit 12 measures the position h in the height direction of the measurement part of the measurement object OB from the output ratio of the first photoelectric conversion surface 32 and the second photoelectric conversion surface 34, similarly to the first exemplary embodiment.

The ROM 16 of the measuring unit 12 stores a table in which the position h in the height direction is correlated with the output ratio or a relational expression of the position h in the height direction and the output ratio, similarly to the first exemplary embodiment. In the measuring device having a configuration equivalent to the configuration illustrated in FIG. 6, in advance, the output values of the first photoelectric conversion surface 32 and the second photoelectric conversion surface 34 are acquired while changing the position h in the height direction of the measurement object OB, the output ratio thereof is calculated, and the table or the relational expression is prepared and stored in the ROM 16.

Figure 7:
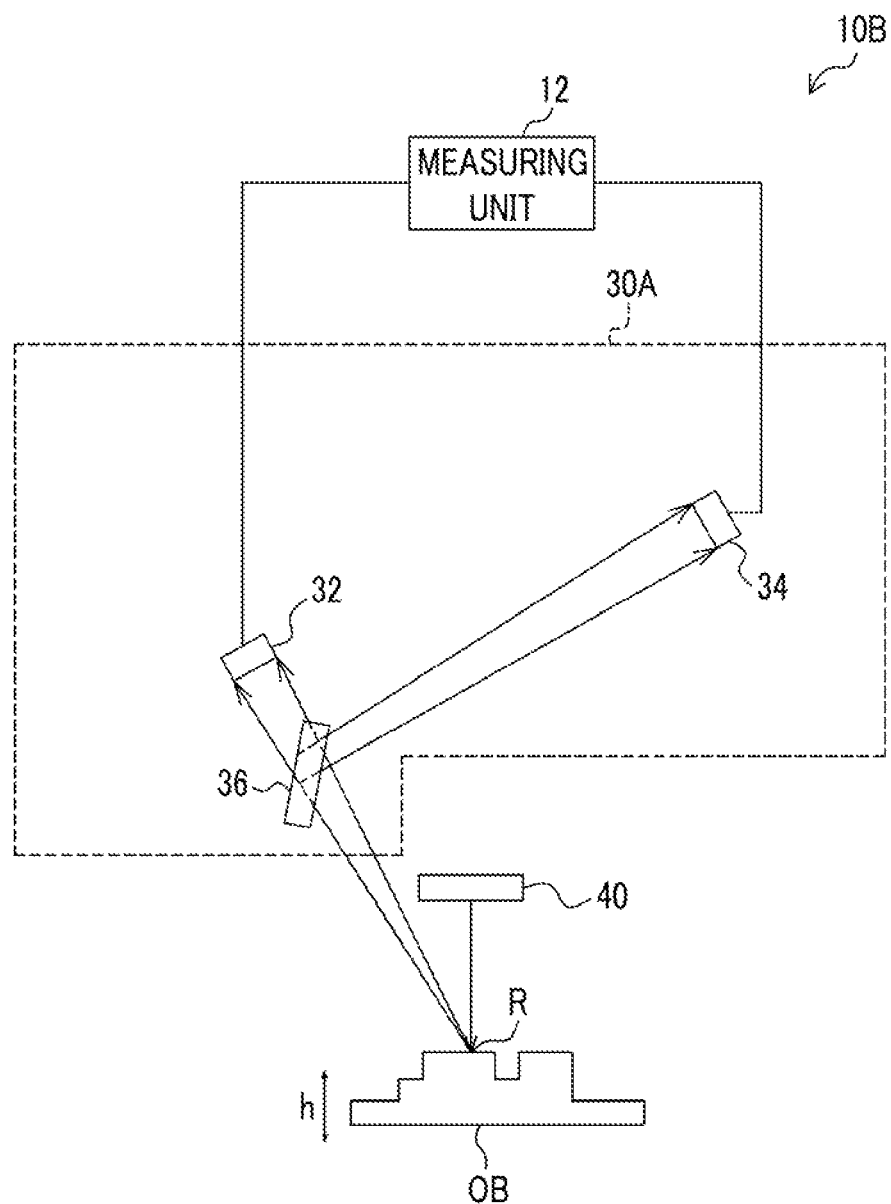
FIG. 7 is a diagram illustrating another example of the configuration of the measuring device according to the second exemplary embodiment.

The light source 40 may be disposed to irradiate the surface (irradiation position with a light beam) of the measurement object OB with a light beam from a direction (substantially normal direction) substantially perpendicular to the surface. In this case, as illustrated in FIG. 7, the arrangement of the first photoelectric conversion surface 32, the second photoelectric conversion surface 34, and the half mirror 36 in the photoelectric conversion unit 30A (the photoelectric conversion unit illustrated in FIG. 7 is referenced by a reference sign 30A, because the arrangement thereof is different from the arrangement of the photoelectric conversion unit 30 illustrated in FIGS. 1 and 6) is set to be different from that in the photoelectric conversion unit 30 illustrated in FIG. 1 or 6. Here, the first photoelectric conversion surface 32, the second photoelectric conversion surface 34, and the half mirror 36 are arranged so as to irradiate the measurement object OB with a light beam from the light source 40 and to receive the reflected light beam (diffused reflected light beam) via the half mirror 36 by the use of the first photoelectric conversion surface 32 and the second photoelectric conversion surface 34. The first photoelectric conversion surface 32 and the second photoelectric conversion surface 34 are disposed to have different optical path lengths until the light beam emitted (reflected) from the measurement object OB is received, similarly to the first exemplary embodiment.

Figure 8:
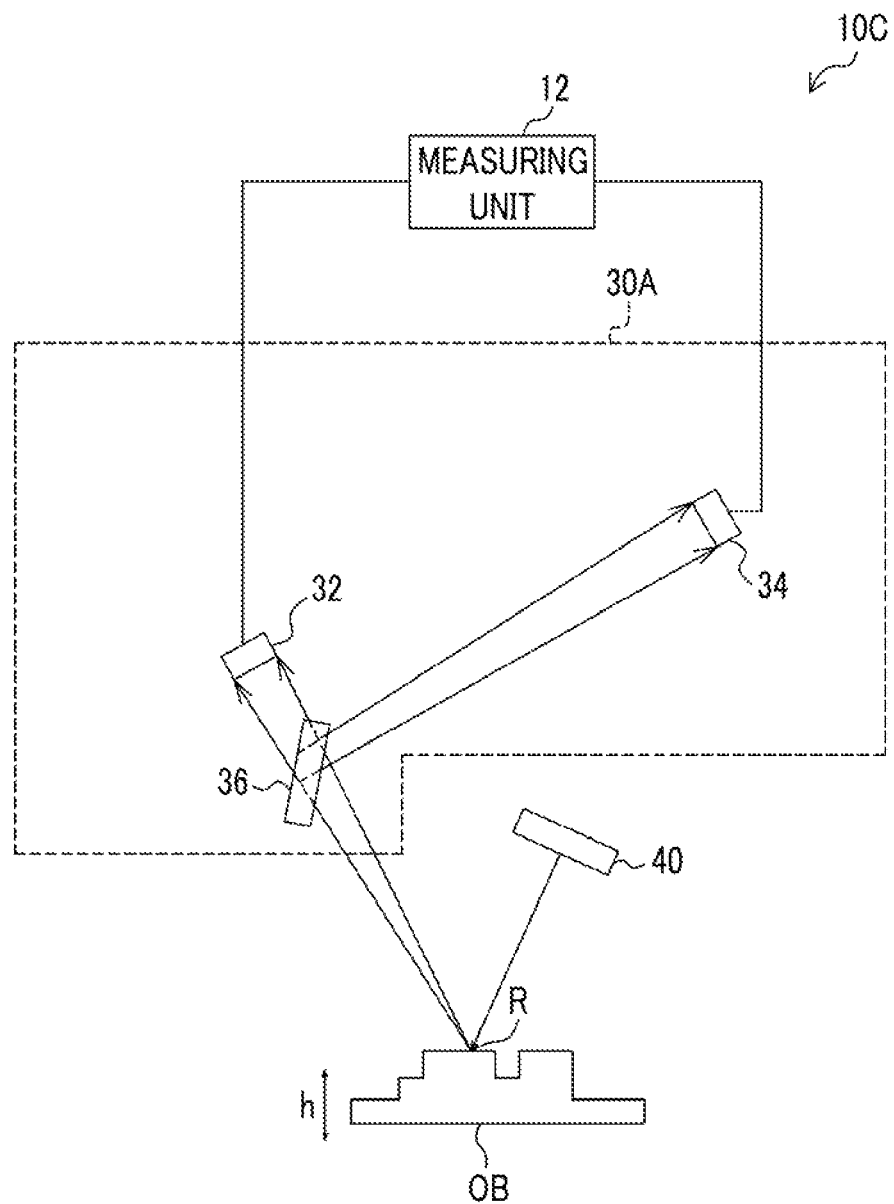
FIG. 8 is a diagram illustrating still another example of the configuration of the measuring device according to the second exemplary embodiment.

As illustrated in FIG. 8, the photoelectric conversion unit 30A is disposed as in a measuring device 10B illustrated in FIG. 7 and the light source 40 is disposed to irradiate the surface (irradiation position with a light beam) of the measurement object OB with a light beam from a direction inclined about the surface. In a measuring device 10C illustrated in FIG. 8, the measurement object OB is irradiated with a light beam in an inclined direction from the light source 40, and the reflected light beam (totally-reflected light beam) is received via the half mirror 36 by the first photoelectric conversion surface 32 and the second photoelectric conversion surface 34.

In this way, the directions of emission and reflection may be arbitrarily set as illustrated in FIGS. 6 to 8, but the irradiation position varies in the horizontal direction with the variation in height of the measurement object OB in the configuration illustrated in FIGS. 6 and 8 and thus the configuration illustrated in FIG. 7 may be preferably employed to avoid this variation.

The number of photoelectric conversion surfaces in the photoelectric conversion units 30 and 30A may be two or three or more. When three or more photoelectric conversion surfaces are provided, two photoelectric conversion surfaces are selected, the output ratio thereof is calculated, and then the position h of the measurement part of the measurement object OB is calculated. Here, when the number of photoelectric conversion surfaces increases, the number of half mirrors also increases and thus light intensity decreases. Accordingly, it is preferable that the number of photoelectric conversion surfaces be as small as possible.

Two or more sets of two photoelectric conversion surfaces for calculating the output ratio may be provided. Accordingly, it is possible to measure or cancel characteristics depending on the difference in emission direction. For example, when a set of photoelectric conversion surfaces for receiving a totally-reflected light beam and a set of photoelectric conversion surfaces for receiving a diffused reflected light beam are provided, it may be also possible to separately measure the totally-reflected light beam and the diffused reflected light beam.

Figure 9:
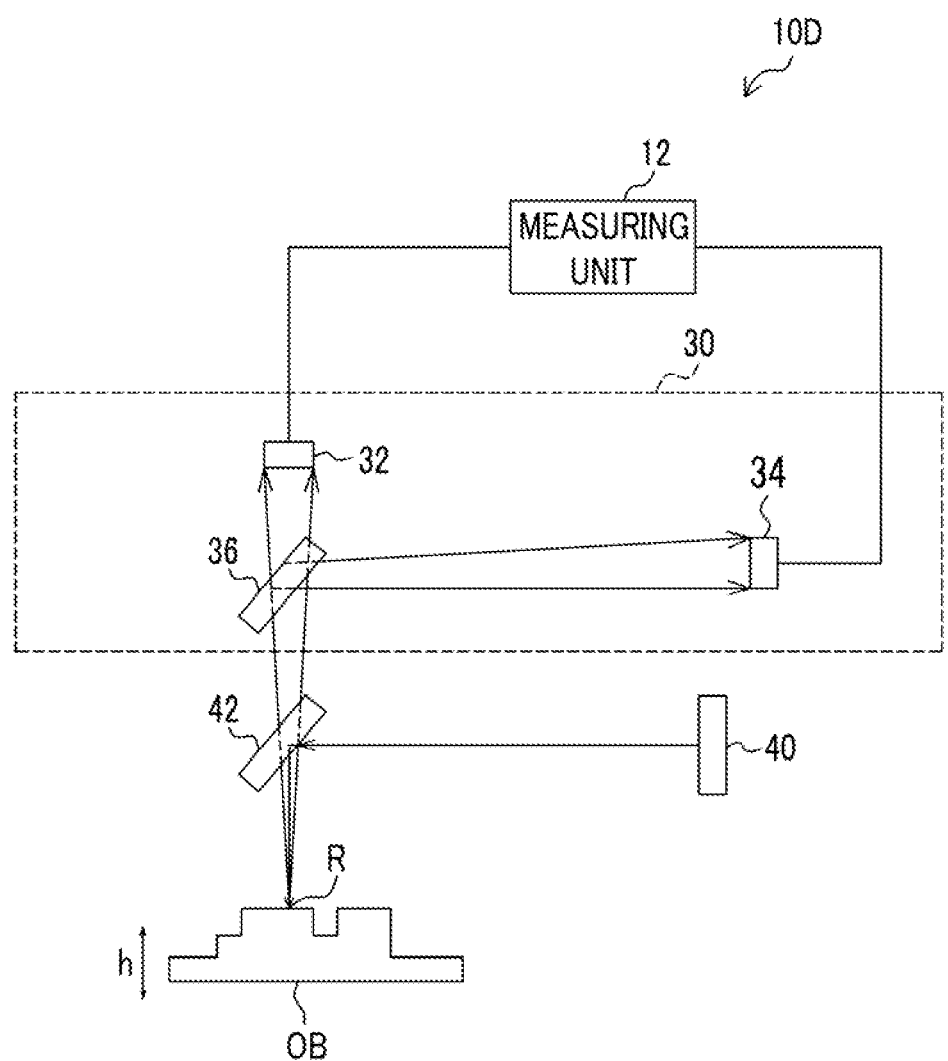
FIG. 9 is a diagram illustrating still another example of the configuration of the measuring device according to the second exemplary embodiment.

A measuring device 10D illustrated in FIG. 9 is configured to receive a reflected light beam reflected in a direction equal to or substantially equal to the irradiation direction of a light beam emitted from the light source 40 and to measure the position h of the reflection point R of the measurement object OB. In the example illustrated in FIG. 9, similarly to FIGS. 1 and 6, the elements of the photoelectric conversion unit 30 are arranged and a half mirror 42 is disposed between the half mirror 36 and the measurement object OB. The light source 40 is disposed at a position at which a light beam may be incident on the half mirror 42. The light beam emitted from the light source 40 is applied to the measurement object OB via the half mirror 42. The reflected light beam reflected from the measurement part (reflection point R) of the measurement object OB is incident on the half mirror 42 again. The half mirror 42 emits the reflected light beam from the measurement object OB to the half mirror 36.

The light beam emitted from the half mirror 42 is incident on the half mirror 36. The half mirror 36 transmits the incident light beam to emit the light beam to the first photoelectric conversion surface 32, and reflects the incident light beam to emit the light beam to the second photoelectric conversion surface 34.

The measuring unit 12 measures the position h of the reflection point R of the measurement object OB as described in the first exemplary embodiment.

Figure 10:
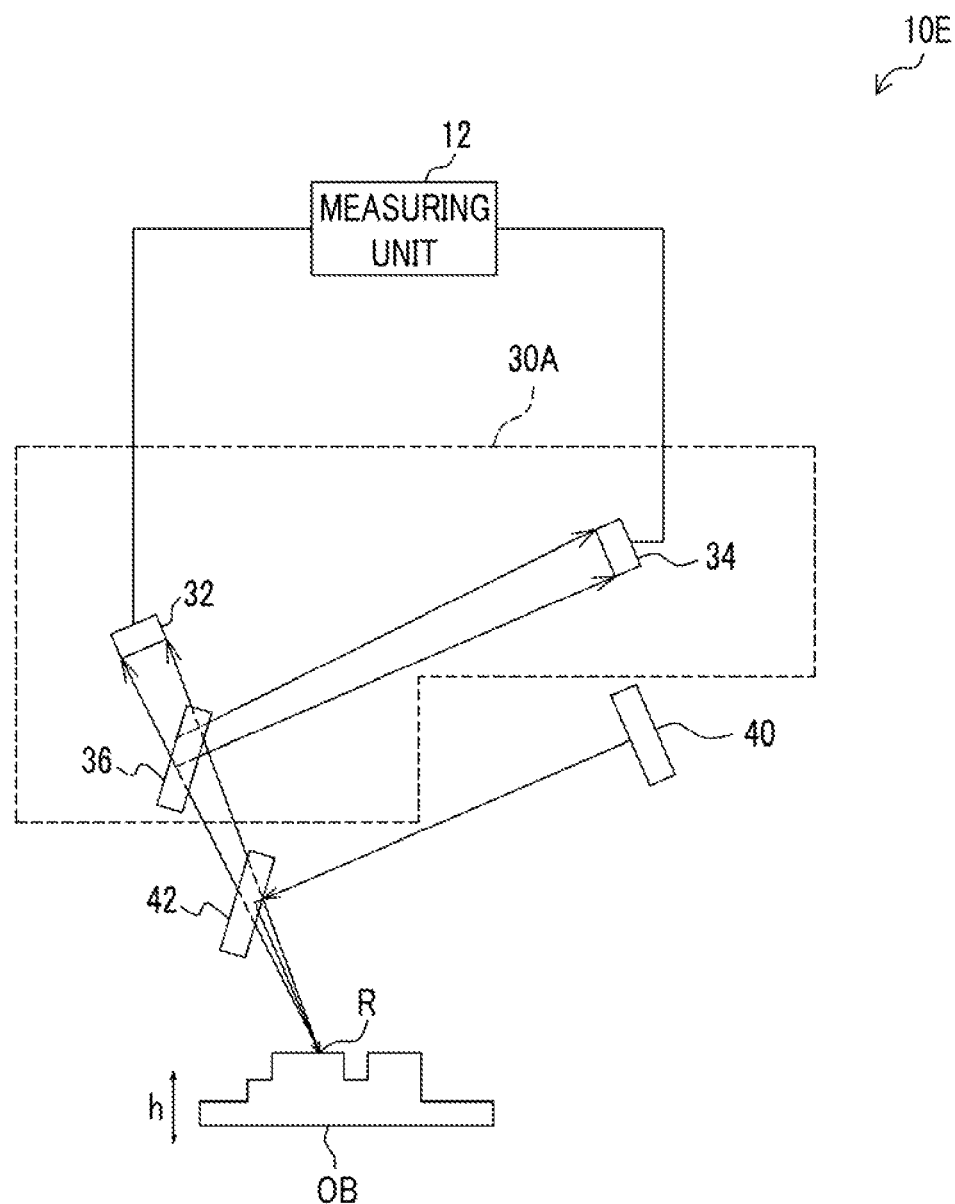
FIG. 10 is a diagram illustrating still another example of the configuration of the measuring device according to the second exemplary embodiment.

In the measuring device 10D illustrated in FIG. 9, the application direction and the reflection direction of a light beam to the measurement part of the measurement object OB are substantially perpendicular (normal) to the measurement part of the measurement object OB, but may not be necessarily perpendicular to the measurement part of the measurement object OB as in a measuring device 10E illustrated in FIG. 10.

Figure 11:
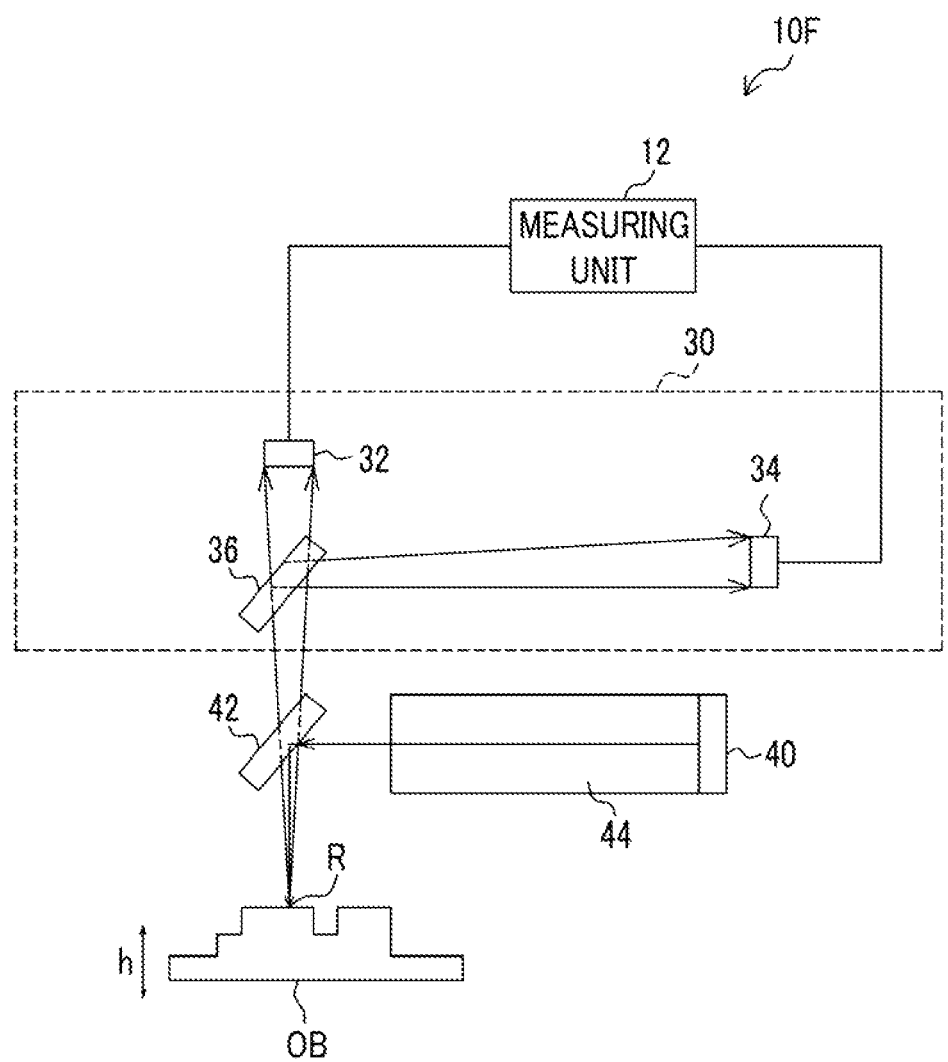
FIG. 11 is a diagram illustrating still another example of the configuration of the measuring device according to the second exemplary embodiment.
Figure 12:
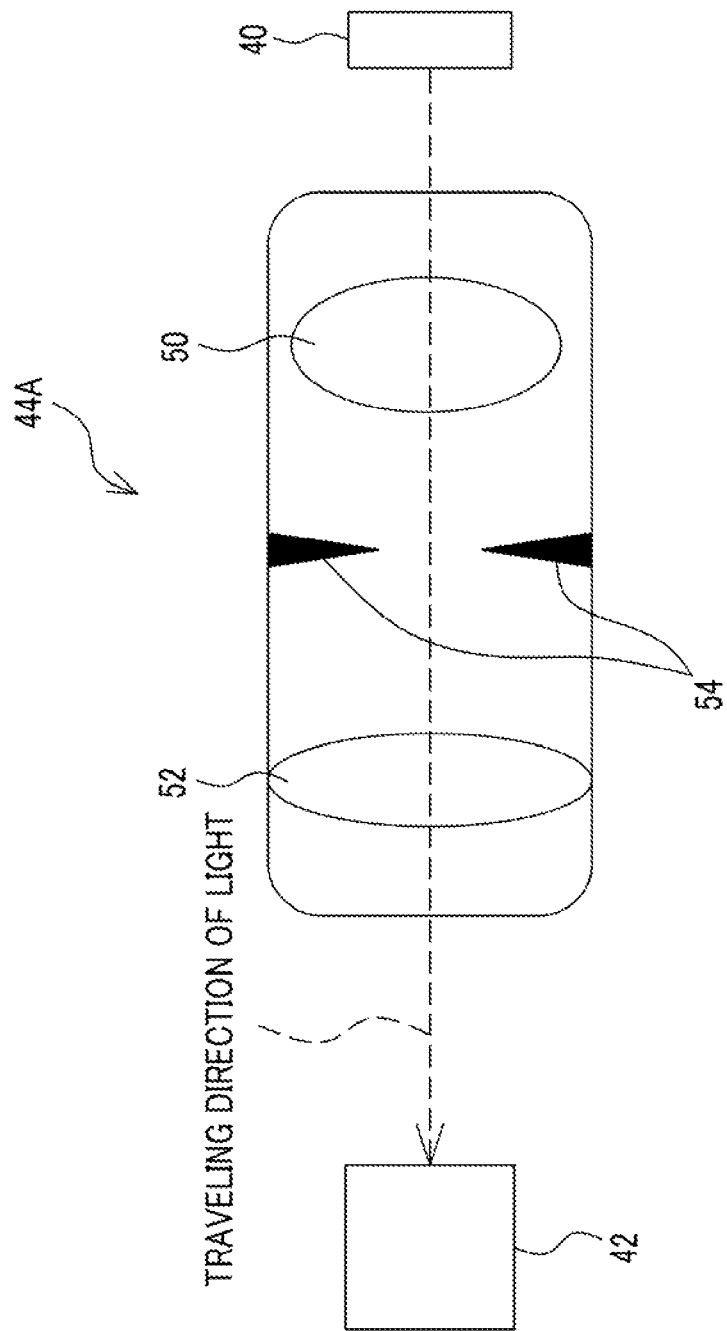
FIG. 12 is a diagram illustrating an example of a configuration of a bi-telecentric lens.

The measuring device may be configured as illustrated in FIG. 11. A measuring device 10F illustrated in FIG. 11 includes a collimator lens 44 in addition to the measuring unit 12, the photoelectric conversion unit 30, the light source 40, and the half mirror 42. The measuring unit 12, the photoelectric conversion unit 30, the light source 40, and the half mirror 42 are arranged similarly to the measuring device 10D described with reference to FIG. 9. The collimator lens 44 is disposed in the optical path from the light source 40 to the half mirror 42. The collimator lens 44 suppresses diffusion of a light beam emitted from the light source 40. For example, a bi-telecentric lens 44A may be used as the collimator lens 44. The bi-telecentric lens 44A includes a pair of lenses 50 and 52 and an iris diaphragm 54 disposed between the pair of lenses 50 and 52 as illustrated in FIG. 12. Achromatic lenses may be used as the two lenses 50 and 52. In this exemplary embodiment, the two achromatic lenses are arranged so that the sides having a smaller curvature face each other. Accordingly, it is possible to reduce aberration of a lens system. The iris diaphragm 54 is disposed to correspond to the focal planes of the lenses 50 and 52. By reducing the size of the iris diaphragm 54, only a parallel light component may be taken but the light intensity is reduced. Accordingly, the size of the iris diaphragm 54 is set depending on necessary accuracy and necessary light intensity.

In any measuring device described in the second exemplary embodiment, the light-receiving areas of the first photoelectric conversion surface 32 and the second photoelectric conversion surface 34 may be equal to each other or different from each other. An example where the light-receiving areas are different from each other will be described in detail in a "third exemplary embodiment" and "various modification examples".

The first exemplary embodiment describes an example where the position h of the emission point P is measured, but the photoelectric conversion unit 30A according to the second exemplary embodiment may be provided instead of the photoelectric conversion unit 30 of the measuring device 10 illustrated in FIG. 1. That is, in the first exemplary embodiment, the photoelectric conversion unit may also be configured to receive a light beam emitted in the inclined direction from the emission point P of the measurement object OB and to photo-electrically convert the received light beam.

Third Exemplary Embodiment

A third exemplary embodiment describes an example where the light-receiving areas of plural photoelectric conversion surfaces of a photoelectric conversion unit are different from each other.

In this exemplary embodiment, elements identical or equivalent to those of the measuring devices 10 to 10F described in the first exemplary embodiment and the second exemplary embodiment will be referenced by the same reference signs and description thereof will not be repeated.

Figure 13:
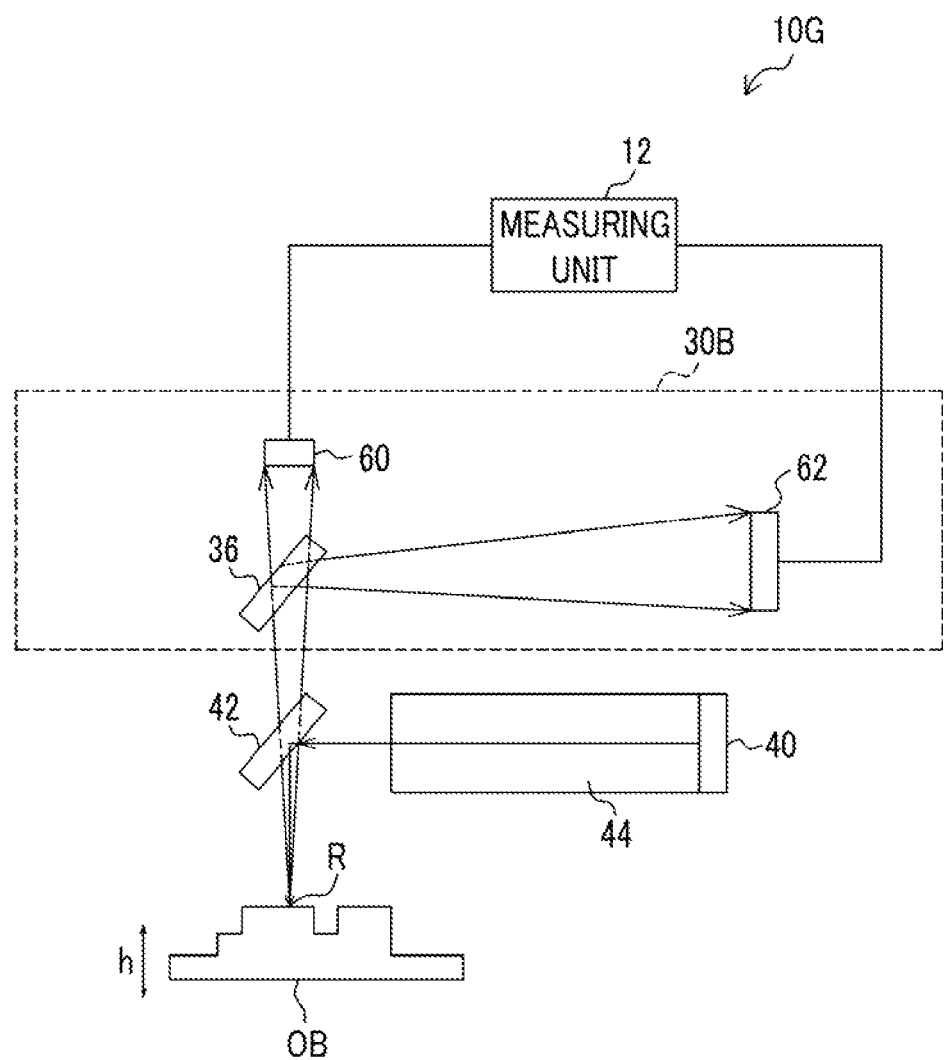
FIG. 13 is a diagram illustrating an example of a configuration of a measuring device according to a third exemplary embodiment.

FIG. 13 illustrates a measuring device 10G according to this exemplary embodiment. As illustrated in FIG. 13, the measuring device 10G includes the measuring unit 12, the photoelectric conversion unit 30B, the light source 40, the half mirror 42, and the collimator lens 44. The measuring device 10G illustrated in FIG. 13 has substantially the same configuration as the measuring device 10F illustrated in FIG. 11, except that the photoelectric conversion unit 30B is provided instead of the photoelectric conversion unit 30.

The photoelectric conversion unit 30B according to this exemplary embodiment includes a first photoelectric conversion surface 60, a second photoelectric conversion surface 62, and the half mirror 36. An imaging device such as a charge coupled device (CCD) or a complementary metal oxide semiconductor (CMOS) may be used as the first photoelectric conversion surface 60 and the second photoelectric conversion surface 62. Here, it is assumed that photodiode (PD) is used.

The light-receiving area of the first photoelectric conversion surface 60 is different from the light-receiving area of the second photoelectric conversion surface 62. Here, the light-receiving area of the photoelectric conversion surface close to the measurement object. OB, that is, the photoelectric conversion surface (first photoelectric conversion surface 60) having a shorter optical path length, is set to be smaller, and the light-receiving area of the photoelectric conversion surface distant from the measurement object OB, that is, the photoelectric conversion surface (second photoelectric conversion surface 62) having a longer optical path length, is set to be larger. For example, various techniques such as making the first photoelectric conversion surface 60 and the second photoelectric conversion surface 62 different from each other in the original size (the size with a maximum light-receivable area) or making the light-receiving areas different from each other using a certain shielding member (see "other embodiments") may be employed for adjustment of the light-receiving area. In this exemplary embodiment, the original sizes of the first photoelectric conversion surface 60 and the second photoelectric conversion surface 62 are made to be different from each other without providing a shielding member or the like. In this exemplary embodiment, a photodiode is used as the first photoelectric conversion surface 60 and the second photoelectric conversion surface 62.

In the measuring device 10G, similarly to the measuring device 10F illustrated in FIG. 11, the measurement object OB is irradiated with a light beam from the light source 40 via the collimator lens 44 and the half mirror 42, and the reflected light beam thereof is received by the first photoelectric conversion surface 60 and the second photoelectric conversion surface 62 via the half mirror 42, and the half mirror 36. The first photoelectric conversion surface 60 and the second photoelectric conversion surface 62 are installed to have different optical path lengths until the light beam emitted (reflected herein) from the measurement object OB is received. The measuring unit 12 measures the position h in the height direction of the measurement part (reflection point R herein) of the measurement object OB based on the output ratio calculated from the output value of the first photoelectric conversion surface 60 and the output value of the second photoelectric conversion surface 62, similarly to the first exemplary embodiment.

The ROM 16 of the measuring unit 12 stores the table in which the position h in the height direction is correlated with the output ratio or the relational expression of the position h in the height direction and the output ratio, similarly to the first exemplary embodiment and the second exemplary embodiment. By employing the measuring device having a configuration equivalent to the configuration illustrated in FIG. 13, in advance, the output values of the first photoelectric conversion surface 60 and the second photoelectric conversion surface 62 are acquired while changing the position h in the height direction of the reflection point R of the measurement, object OB, the output ratio thereof is calculated, and the table or the relational expression is prepared and stored in the ROM 16.

The measuring unit 12 measures the position h in the height direction of the reflection point R, based on the output ratio of two electrical signals with reference to the table or the relational expression stored in the ROM 16.

Figure 14:
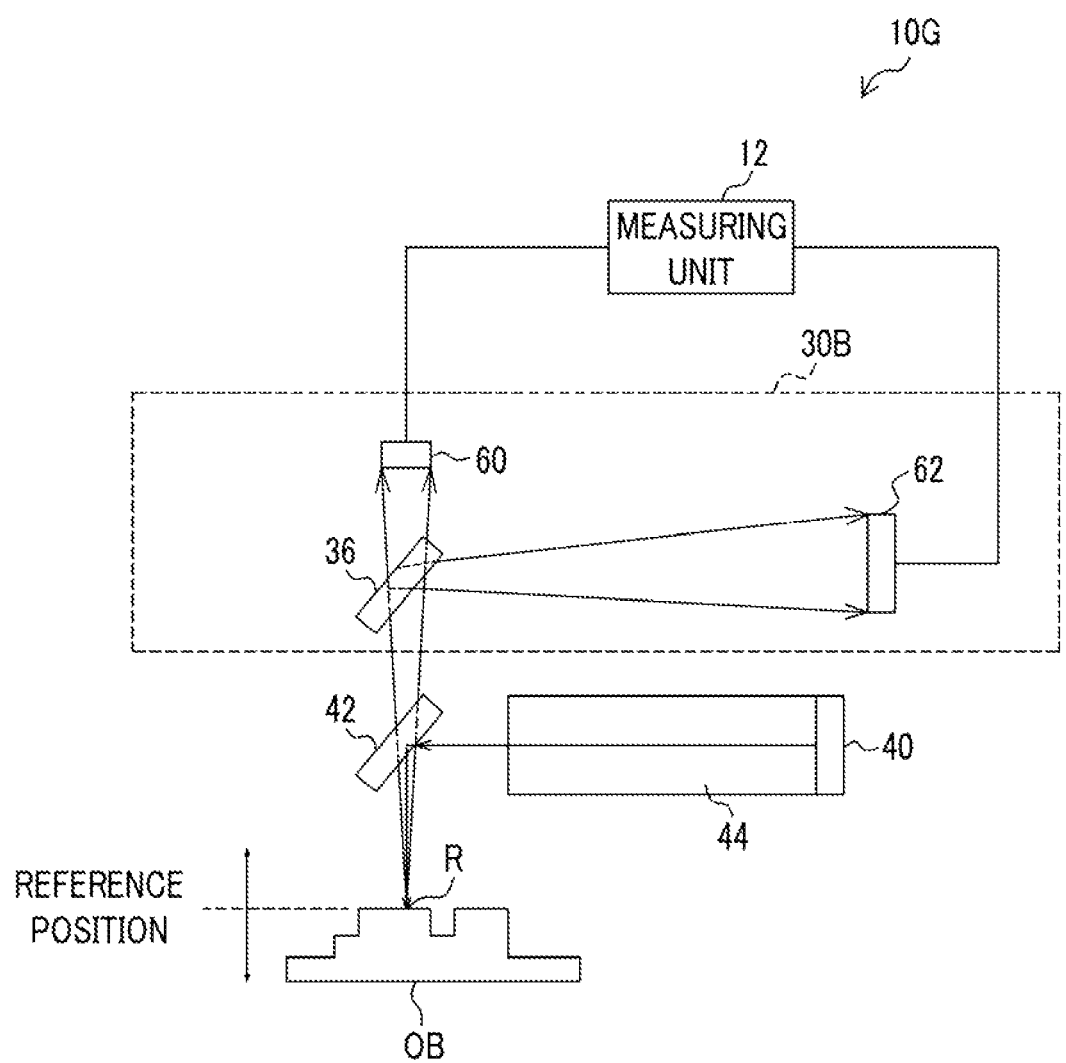
FIG. 14 is a diagram illustrating a reference position set in the height direction of a measurement object.

As illustrated in FIG. 14, a reference position in the height direction of a measurement target may be set in advance. A displacement from the reference position may be measured as the position h.

Here, the first photoelectric conversion surface 60 and the second photoelectric conversion surface 62 are installed so that when the position h in the height direction of the measurement target is the reference position, the light intensities incident on the first photoelectric conversion surface 60 and the second photoelectric conversion surface 62 are equivalent to the ratio of transmitted light/reflected light of the half mirror 36 (when correction is completed so that the transmitted/reflected light beams are 50% and the sensitivities of the first photoelectric conversion surface 60 and the second photoelectric conversion surface 62 are equal to each other, the output values of the first photoelectric conversion surface 60 and the second photoelectric conversion surface 62 are equal to each other and the output ratio thereof is 1).

Figure 15:
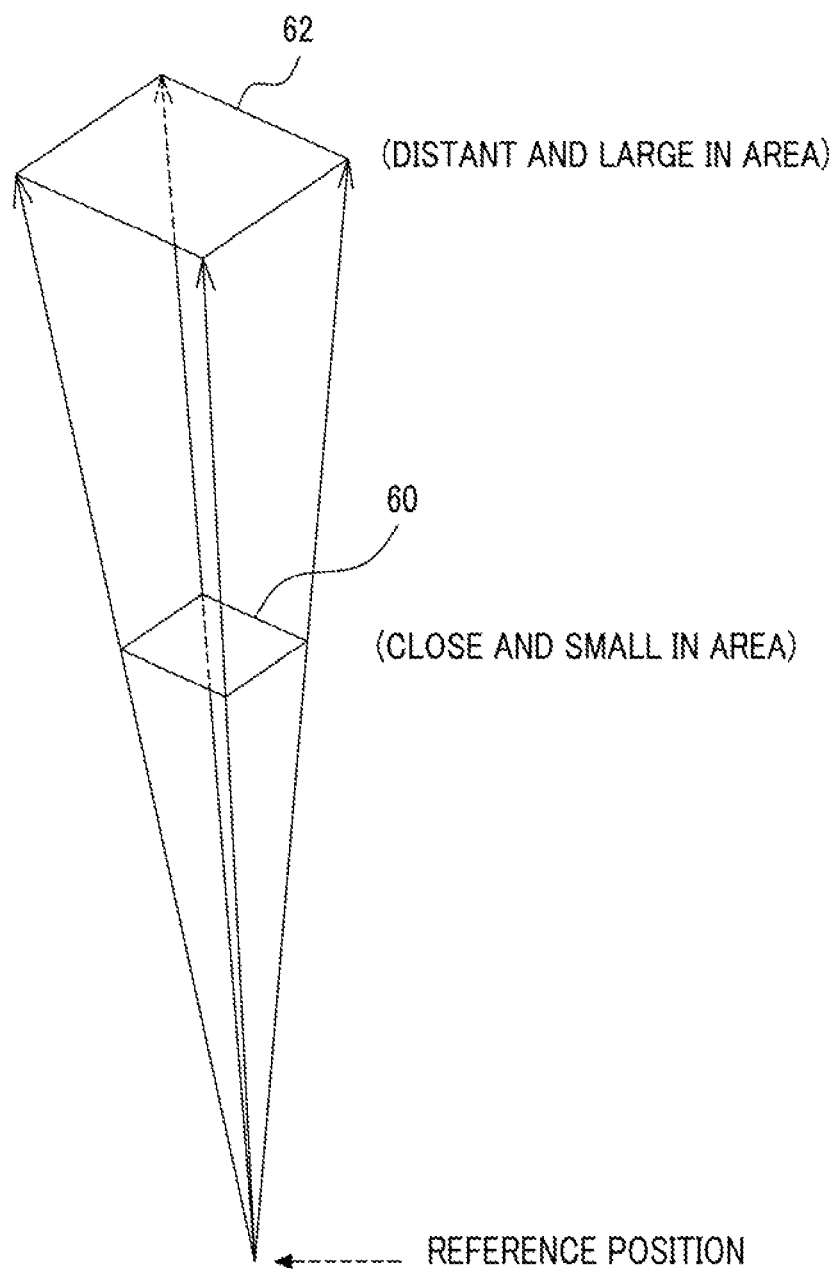
FIG. 15 is a diagram illustrating a reference position.

The reference position will be described in more detail with reference to the schematic diagram illustrated in FIG. 15. FIG. 15 is a diagram schematically illustrating a light beam incident on the first photoelectric conversion surface 60 from the reflection point R of the measuring device 10G and a light beam incident on the second photoelectric conversion surface 62 from the reflection point R in an overlapping manner. As illustrated in FIG. 15, the photoelectric conversion surfaces are disposed so that the reflected light beam passing through the outer edge of the first photoelectric conversion surface 60 out of the reflected light beam from the reference position also passes through the outer edge of the second photoelectric conversion surface 62. Here, since the first photoelectric conversion surface 60 and the second photoelectric conversion surface 62 are rectangular, each outer edge includes vertices and sides. In this arrangement, when a light beam emitted from the reference position is received by the first photoelectric conversion surface 60 and the second photoelectric conversion surface 62, the output ratio thereof is 1.

Figure 16:
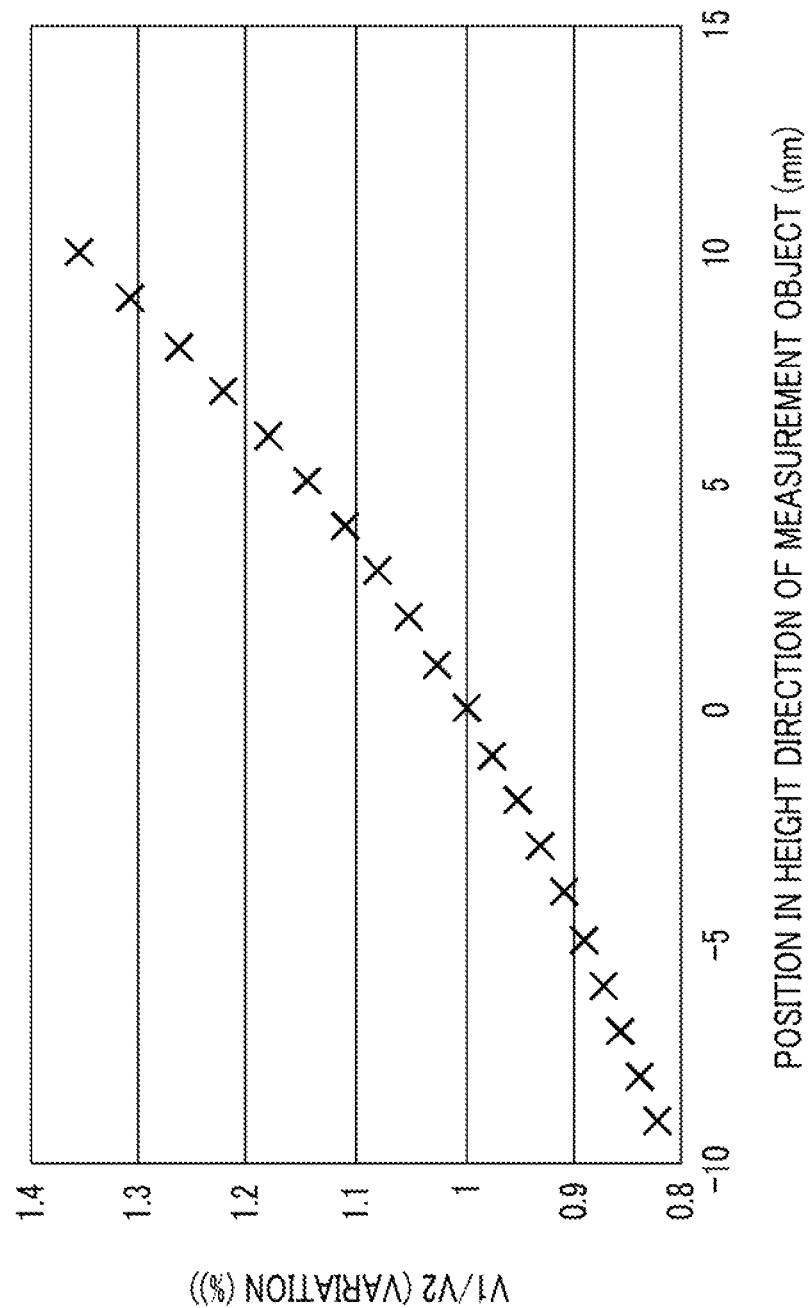
FIG. 16 is a graph illustrating an example of a relationship between an output ratio of a first photoelectric conversion surface and a second photoelectric conversion surface and a position of a reflection point (measurement target) of a measurement object.

FIG. 16 is a graph illustrating an example of the relationship between the output ratio of the first photoelectric conversion surface 60 and the second photoelectric conversion surface 62 and the position h of the reflection point R (measurement target) of the measurement object OB. In this example, it is assumed that the reflected light beam from the measurement object OB is a completely-diffused reflected light beam. The horizontal axis represents the position h in the height direction of the reflection point R of the measurement object OB (the reference position is set to 0, the direction in which the position is farther (lower) from the photoelectric conversion unit than the reference position is set to be minus, and the direction in which the position is closer (higher) to the photoelectric conversion unit than the reference position is set to be plus), and the vertical axis represents the ratio V1/V2 (variation %) of the output value V1 of the first photoelectric conversion surface 60 and the output value V2 of the second photoelectric conversion surface 62. Since the graph is a curve, the position h in the height direction of the measurement target may be calculated from the output ratio V1/V2 by preparing an approximate expression to the curve or preparing a table indicating the correlation. The graph illustrated in FIG. 16 is a graph when the photoelectric conversion unit 30B is installed to correspond to the reference position as illustrated in FIG. 15 using the configuration of the measuring device 10G illustrated in FIG. 14. When the horizontal axis is equal to 0, the vertical axis is equal to 1, that is, the output values of the first photoelectric conversion surface 60 and the second photoelectric conversion surface 62 are equal to each other.

By constructing the first photoelectric conversion surface 60 and the second photoelectric conversion surface 62 of the photoelectric conversion unit 30B in this way, a light beam within the same angle range is received at the reference position even when there is a deviation in a light intensity distribution of a reflected light beam. Accordingly, there is an advantage that a measurement error is reduced even when the position h varies from the reference position.

An example where the output ratio is set to 1 is described above, but the output ratio may be set to be substantially 1 (within a predetermined range including 1).

The photoelectric conversion unit has only to be configured so that the difference between the optical path lengths from the reference position to two photoelectric conversion surfaces is equal to or greater than a predetermined value in a state where the measurement target is disposed at the reference position. This is because when the difference is excessively small, the position h may not be measured. Therefore, the photoelectric conversion unit is configured so that the difference between the optical path lengths is equal to or more than a value suitable for measuring a position. For example, when the photoelectric conversion unit is configured so that the difference between the optical path lengths from the reference position to two photoelectric conversion surfaces is equal to or more than 5% of the smaller optical path length, it is possible to satisfactorily measure the position h. More strictly, a lower limit value of the difference suitable for measuring the position h is acquired as the difference between the optical path lengths in advance by experiments or the like and the photoelectric conversion unit may be configured so that the difference between the optical path lengths is equal to or more than the lower limit value.

An example where the collimator lens 44 is provided in all the measuring devices 10A to 10G is described above, but the collimator lens 44 may not be provided.

The light source 40 included in the measuring devices 10A to 10G is described to be a light source for emitting a light beam from one emission point disposed in the light source 40, but the present invention is not limited to this configuration. For example, a light source for emitting a light beam to the measurement object OB may include plural emission points and a light beam may be sequentially emitted from the emission points.

FIG. 17 illustrates a measuring device 10H including a light source having plural emission points. The measuring device 10H includes the measuring unit 12, the photoelectric conversion unit 30B, a light source 46, the collimator lens 44, and the half mirror 42.

The photoelectric conversion unit 30B is the same as the photoelectric conversion unit 30B of the measuring device 10G illustrated in FIG. 13.

The light source 46 is configured to have plural emission points arranged at substantially identical intervals and to sequentially emit plural light beams. The irradiation angles of the plural light beams are substantially equal to each other. For example, the light source 46 may employ a semiconductor laser having plural emission points or an LED array having plural LEDs arranged therein. Specifically, an edge emitting laser (EEL) may be used as the semiconductor laser, and a vertical cavity surface emitting laser (VCSEL) may be used. In this example, it is assumed that the VCSEL is used and plural light beams are emitted as irradiation light beams from the VCSEL.

Light beams are sequentially emitted from the emission points of the light source 46 of the measuring device 10H. Each light beam is applied to the measurement object OB via the collimator lens 44 and the half mirror 42, and the reflected light beam thereof is received by the first photoelectric conversion surface 60 and the second photoelectric conversion surface 62 via the half mirror 42 and the half mirror 36. The measuring unit 12 measures the position h in the height direction of the measurement part (reflection point R) of the measurement object OB for each light beam based on the output ratio calculated from the output value of the first photoelectric conversion surface 60 and the output value of the second photoelectric conversion surface 62. The irradiation regions of the light beams in the measurement object OB are designed so as not to overlap with each other or so that the overlapping area is less than a predetermined area even when the irradiation regions overlap with each other. Accordingly, it is possible to measure the position h (that is, to measure the unevenness state of the surface of the measurement object OB) for each light beam (that is, for each irradiation region), and to measure the position so that the measured values are independent of each other.

The measurement object OB may be installed so that the irradiation position of the measurement object OB with a light beam emitted from one emission point selected from plural emission points is matched with the reference position and then the measurement may be performed. For example, as illustrated in the enlarged view (schematic diagram) of FIG. 17, the irradiation position with the light beam emitted from the emission point located at the center of the plural emission points is matched with the reference position.

In this case, since plural irradiation light beams in addition to the irradiation light beam applied to the reference position are applied in parallel in the horizontal direction, reflected light beams from positions other than the reference position are formed. Here, by setting the central irradiation light beam out of the plural irradiation light beams to the reference position, it is possible to acquire a difference from the reference position as the measured value of each irradiation position and thus to suppress the measurement error as much as possible.

In this configuration, the collimator lens 44 may not be provided, but the collimator lens 44 provides the following advantages. These advantages will be described below with reference to FIG. 18.

Figure 18:
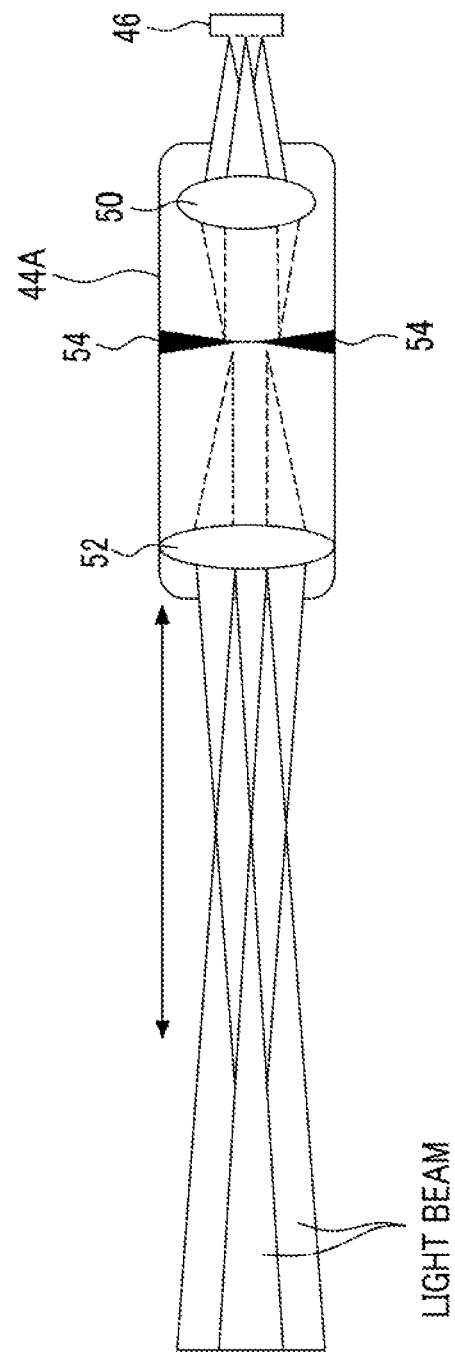
FIG. 18 is a diagram schematically illustrating a state where plural light beams are emitted from a light source when the bi-telecentric lens illustrated in FIG. 12 is used as a collimator lens of the measuring device illustrated in FIG. 17.

FIG. 18 is a diagram schematically illustrating a state where plural light beams are emitted from the light source 46 when the bi-telecentric lens 44A illustrated in FIG. 12 is used as the collimator lens 44 of the measuring device 10H.

As described above, the bi-telecentric lens 44A includes the pair of lenses 50 and 52 and the iris diaphragm 54 disposed between the pair of lenses 50 and 52. Achromatic lenses may be used as the two lenses 50 and 52 to arrange the two achromatic lenses so that the sides having a smaller curvature face each other. Accordingly, it is possible to reduce aberration of a lens system. The iris diaphragm 54 is disposed to correspond to the focal planes of the lenses 50 and 52.

As described above, it is preferable that the measurement object OB be disposed in a range in which the irradiation regions of the light beams from the neighboring emission points of the light source 46 do not overlap with each other. This is because when the light beams are sequentially emitted from the respective emission points but the overlapping area of the irradiation regions of the neighboring light beams on the measurement object OB increases, the output values are not independent of each other. In FIG. 18, for example, the irradiation regions of the neighboring light beams do not overlap with each other in the range indicated by an arrow. Therefore, the measurement part of the measurement object OB may be located in the range.

The light source 46 may be preferably disposed on the focal plane of the lens 50 closer to the light source 46 in the bi-telecentric lens 44A. Accordingly, the light beam passing through the iris diaphragm 54 becomes a parallel light beam and it is thus possible to reduce an error of the irradiation angle due to the positional difference of the iris diaphragm 54.

A part (for example, light beams of emission points at both ends out of plural emission points arranged in a predetermined direction or emission points in a predetermined range including the emission points at both ends) of plural light beams emitted from the emission points of the light source 46 may be set as visible rays. Accordingly, the measurement range may be visually recognized.

The third exemplary embodiment is described above with reference to multiple examples where the light-receiving areas of plural photoelectric conversion surfaces are different from each other, and the respective examples may be similarly applied to the measuring device 10 not including a light source as illustrated in FIG. 1. That is, the light beam received by the photoelectric conversion unit according to the third exemplary embodiment may be an emitted light beam or a reflected light beam from the measurement object OB.

The configuration in which a light beam is emitted from the light source 46 including plural emission points to perform measurement may be applied to the measuring devices described in the second exemplary embodiment.

VARIOUS MODIFICATION EXAMPLES

A measuring device may have various configurations to be described below in addition to the configurations described in the first, second, and third exemplary embodiments.

Modification Example 1

In the first exemplary embodiment, the measuring device 10 that receives an emitted light beam from the emission point P of the measurement object OB and measures the position h in the height direction of the emission point P is described above. In the second and third exemplary embodiments, the measuring devices 10A to 10H that receive a reflected light beam of the light beam applied to the measurement object OB from the light source and measure the position h in the height direction of the reflection point R of the measurement object OB are described above.

However, the measurement targets of the measuring devices are not limited to the emission point or the reflection point. For example, a position h in the height direction of a condensation point may be measured using the condensation point as a measurement target.

Figure 19:
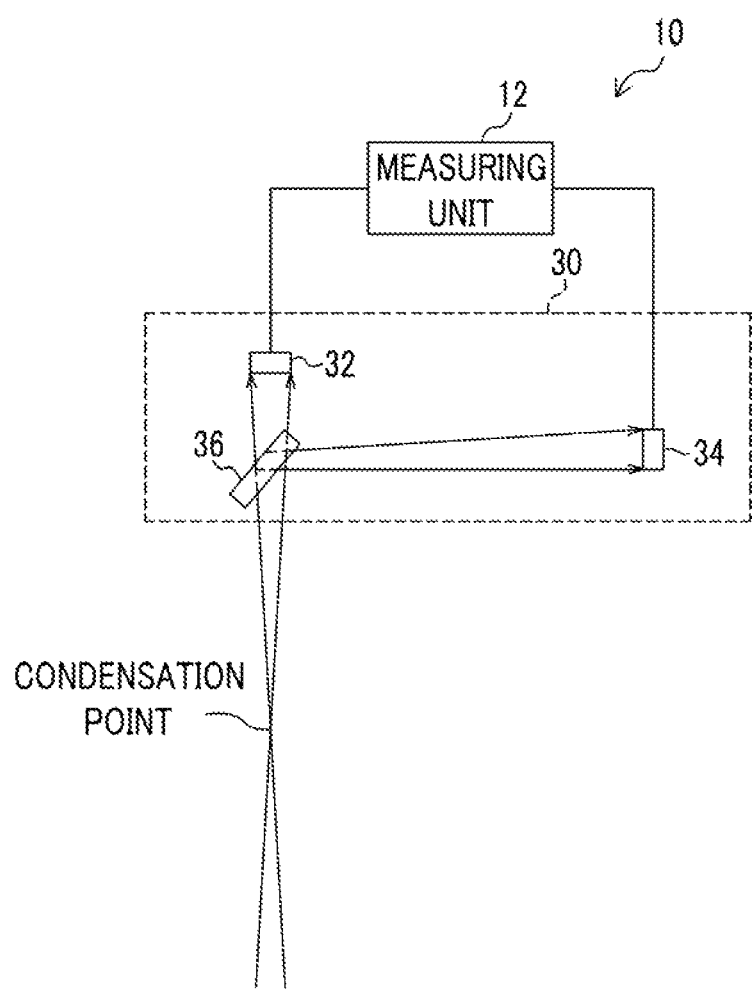
FIG. 19 is a diagram illustrating an example where a measurement target of a measuring device is a condensation point.

That is, for example, the emission point P in FIG. 1 is used as the measurement target in the first exemplary embodiment, but a condensation point of a light beam which is temporarily condensed and then diffused may be used as the measurement target as illustrated in FIG. 19. For example, the measurement target may be a condensation point which is temporarily condensed and then diffused, similarly to the reflection point R used as the measurement target in the second or third exemplary embodiment. In this way, even when a condensation point is measured, the measuring devices described in the first to third exemplary embodiments may be applied to measure the position h of a point at which a light beam is condensed in a space, instead of an emission point or a reflection point which is physically present.

Modification Example 2

At least one of the photoelectric conversion surfaces (for example, the first photoelectric conversion surfaces 32 and 60 and the second photoelectric conversion surfaces 34 and 62) provided to the above-mentioned measuring devices 10 to 10H may be provided with a shielding member that blocks a light beam incident on each photoelectric conversion surface by limiting the light-receiving area of the corresponding photoelectric conversion surface.

In this modification example and modification examples to be described later, when the photoelectric conversion surfaces such as the first photoelectric conversion surfaces 32 and 60 and the second photoelectric conversion surfaces 34 and 62 are used without being distinguished, the photoelectric conversion surfaces are generically referred to as photoelectric conversion surfaces and are referenced by reference numeral 80 (90 in Modification Example 7). When plural photoelectric conversion surfaces are described to be distinguished from each other, subscripts 1, 2, 3, . . . may be added to reference numeral 80 (90 in Modification Example 7). A photoelectric conversion surface 80 may be a PD, or an array in which plural PDs are arranged, or an imaging device such as a CCD or a CMOS.

Figure 20:
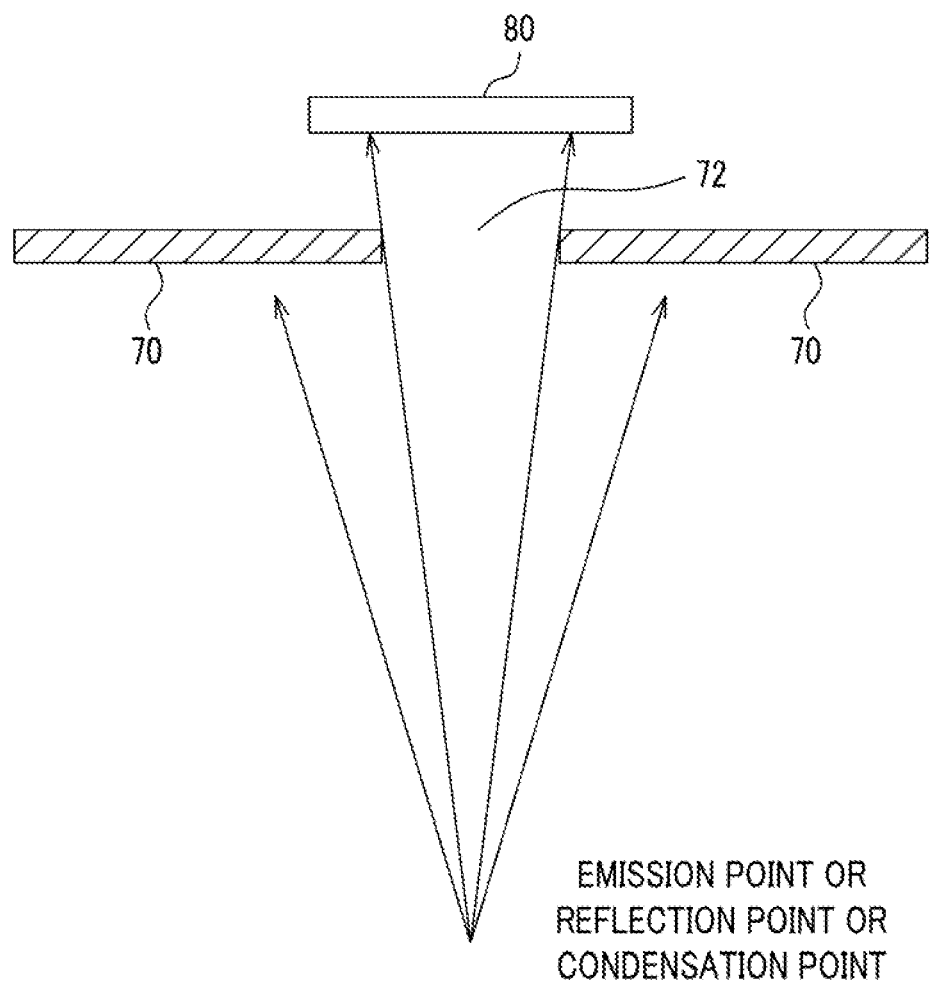
FIG. 20 is a diagram schematically illustrating an exemplary embodiment in which a photoelectric conversion surface is provided with a shielding member partially blocking a light beam incident on the photoelectric conversion surface.

FIG. 20 is a diagram schematically illustrating an exemplary embodiment in which the photoelectric conversion surface 60 is provided with a shielding member 70 partially blocking a light beam incident on the photoelectric conversion surface 80. The shielding member 70 is provided with an opening 72 and the light beam passing through the opening 72 of the shielding member 70 reaches the photoelectric conversion surface 80.

The photoelectric conversion surfaces included in the measuring devices 10 to 10H described in the first to third exemplary embodiments have two functions of receiving only a light beam in a specific region out of diffused light beams (the reception of light is limited by adjusting the original sizes of the photoelectric conversion surfaces in the exemplary embodiments) and photo-electrically converting the light beam incident on the specific region, but the functions may be embodied by two members of the shielding member 70 and the photoelectric conversion surface 80 as illustrated in FIG. 20.

Figure 21:
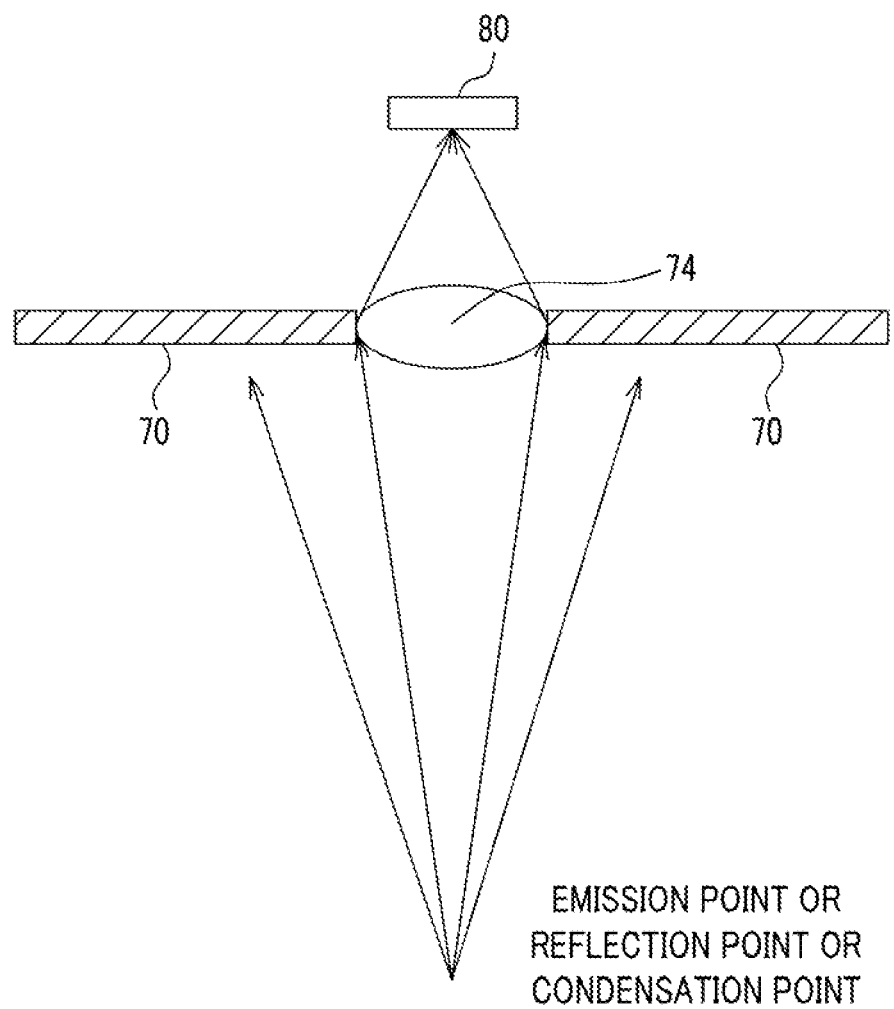
FIG. 21 is a diagram schematically illustrating an example of a configuration in which a lens is installed in an opening of the shielding member illustrated in FIG. 20.

As illustrated in FIG. 21, a lens 74 may be disposed in the opening of the shielding member 70. When the original size of the photoelectric conversion surface 80 is small, a light beam incident on the photoelectric conversion surface 80 may be reduced and then be incident on the photoelectric conversion surface 80 with the small size by providing the opening of the shielding member 70 with the lens 74.

Modification Example 3

Figure 22:
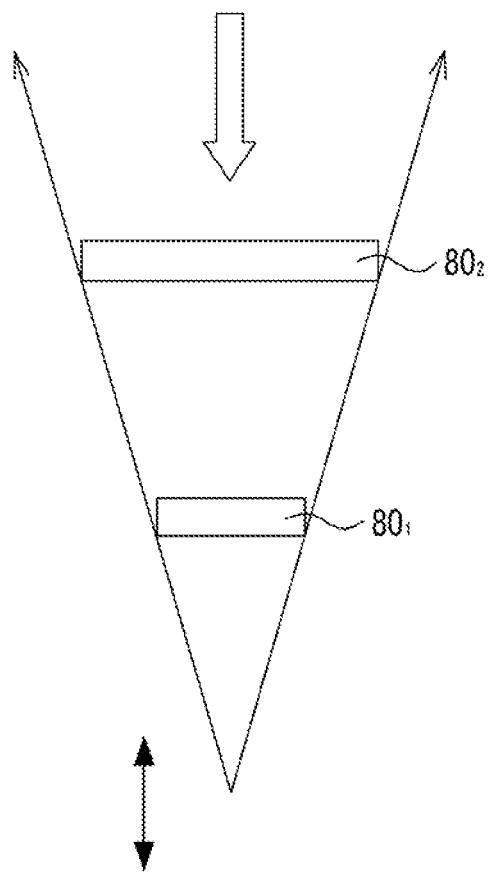
FIG. 22 is a diagram schematically illustrating an example of a configuration in which at least one of two photoelectric conversion surfaces is movable.

FIG. 22 illustrates an example where at least one of two photoelectric conversion surfaces $80_1$ and $80_2$ is configured to be movable. In this example, a moving mechanism (not illustrated) that vertically moves at least one photoelectric conversion surface 80 is provided and the moving mechanism is controlled to move the photoelectric conversion surface 80 by the use of the CPU 14 of the measuring unit 12. Here, the half mirror and reflection of a light beam from the half mirror are not illustrated.

When it is necessary to measure a position with high accuracy, it is preferable that the positional relationship between the two photoelectric conversion surfaces $80_1$ and $80_2$ be adjusted so that the center of the position variation range of the measurement target is located at the reference position (see FIG. 15).

Accordingly, as illustrated in FIG. 22, at least one photoelectric conversion surface 80 is configured to be movable. Specifically, for example, a support member supporting the photoelectric conversion surface 80 is provided with the moving mechanism and the position of the photoelectric conversion surface 80 is adjusted by controlling the moving mechanism. The position adjustment control is performed by the CPU 14 of the measuring unit 12.

For example, when the variation range of the position h of the measurement target is shifted in the direction so as to get closer to the photoelectric conversion surface 80 (the variation range rises), the adjustment is performed as illustrated in FIG. 22. That is, the photoelectric conversion surface $80_2$ is moved to be closer to the photoelectric conversion surface $80_1$.

In addition to the configuration of changing the light-receiving position illustrated in this modification example, another configuration of adjusting the position of the photoelectric conversion surface so that the center of the position variation range of the measurement target is located at the reference position will be described below in Modification Example 4.

Modification Example 4

The light-receiving region of at least one of the two photoelectric conversion surfaces $80_1$ and $80_2$ may be changed.

Figure 23:
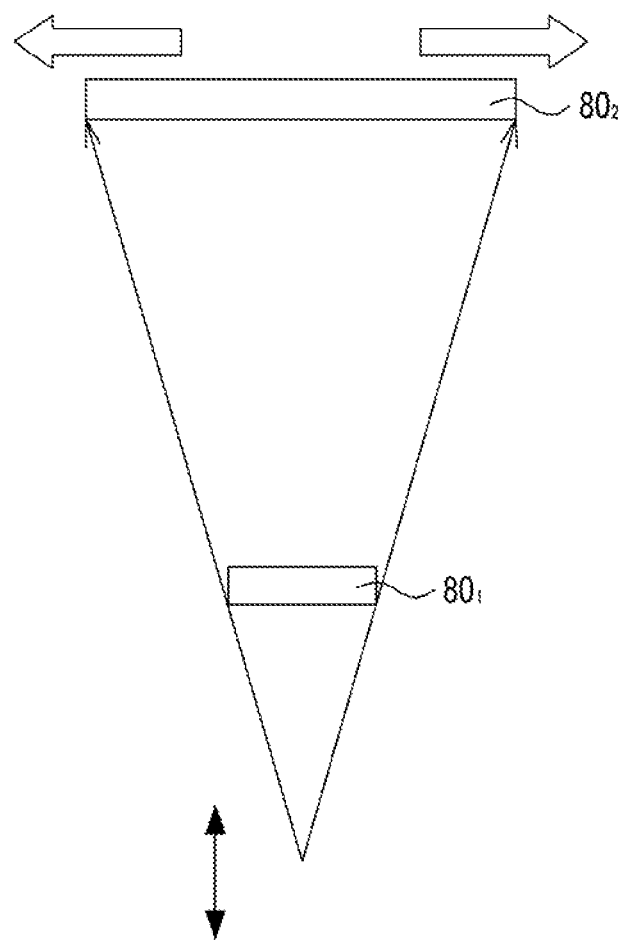
FIG. 23 is a diagram schematically illustrating an example of a configuration in which a light-receiving region of at least one of two photoelectric conversion surfaces may be changed.

FIG. 23 is a diagram schematically illustrating an example of a configuration in which the light-receiving region of at least one of the two photoelectric conversion surfaces $80_1$ and $80_2$ may be changed. For example, when the variation range of the position h of the measurement target varies in the direction in which it gets closer to the photoelectric conversion surface 80 (when the variation range rises), the light-receiving region is adjusted to increase the light-receiving area as illustrated in FIG. 23.

A specific example of a configuration for changing the light-receiving region will be described below.

Figure 24:
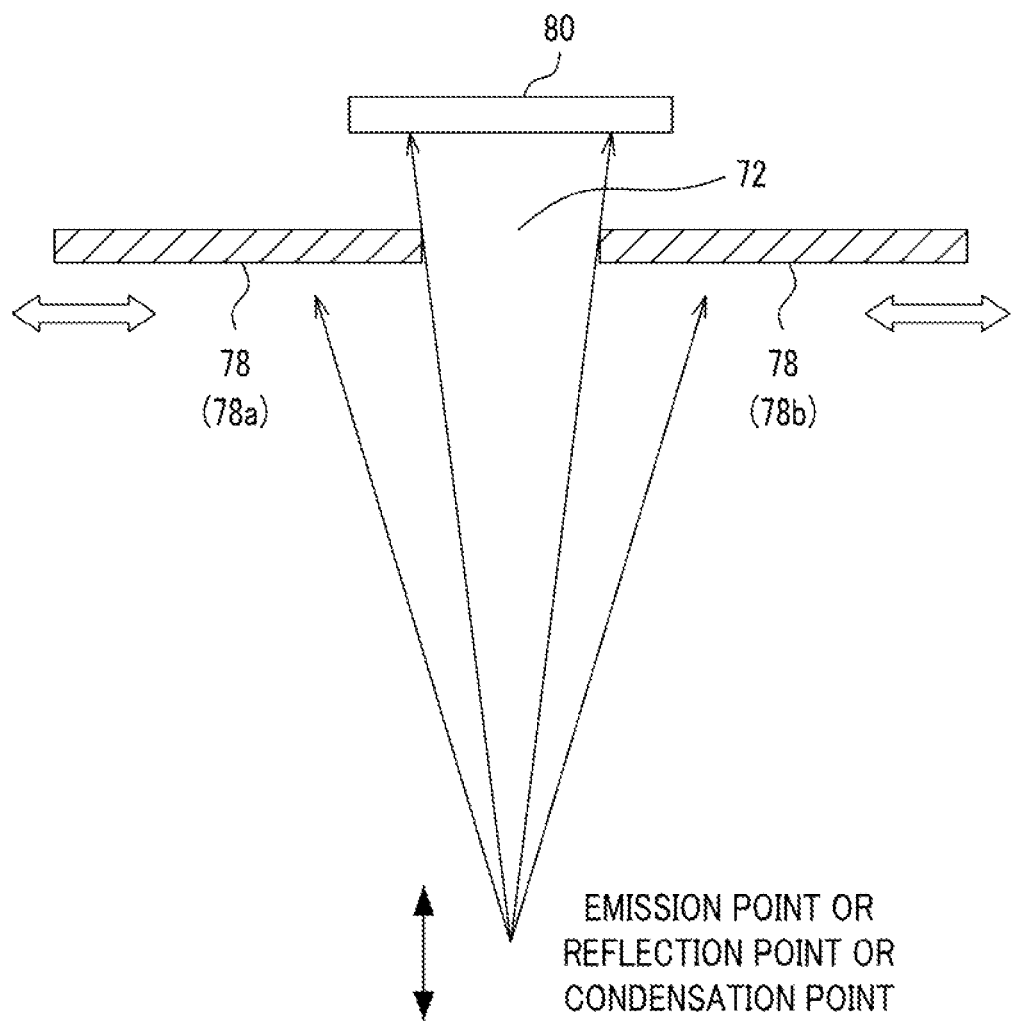
FIG. 24 is a diagram schematically illustrating an exemplary embodiment in which a photoelectric conversion surface is provided with a movable shielding member partially blocking a light beam incident on the photoelectric conversion surface.

FIG. 24 is a diagram schematically illustrating an exemplary embodiment in which the photoelectric conversion surface 80 is provided with a movable shielding member 78 partially blocking a light beam incident on the photoelectric conversion surface 80.

The shielding member 78 is provided with the opening 72 and a light beam passing through the opening 72 of the shielding member 78 reaches the photoelectric conversion surface 80. Respective members 78a and 78b of the shielding member 78 are configured to be movable in the horizontal direction. For example, a support member supporting the members 78a and 78b is provided with a moving mechanism moving in the horizontal direction relative to the light-receiving surface of the photoelectric conversion surface 80, and the area of the opening 72 is adjusted by controlling the moving mechanism. The movement of the moving mechanism is controlled by the CPU 14 of the measuring unit 12.

The photoelectric conversion surface 80 may be formed of an imaging device having plural light receiving portions. The light-receiving region may be electronically selected using the imaging device. The imaging device may be a set of PDs. More specifically, a PD unit in which plural PDs are arranged may be provided as the photoelectric conversion surface 80, the PDs receiving a light beam out of the PDs of the PD unit may be selected, and the outputs of the selected PD may be acquired. Accordingly, the light-receiving area may be adjusted.

Figure 25:
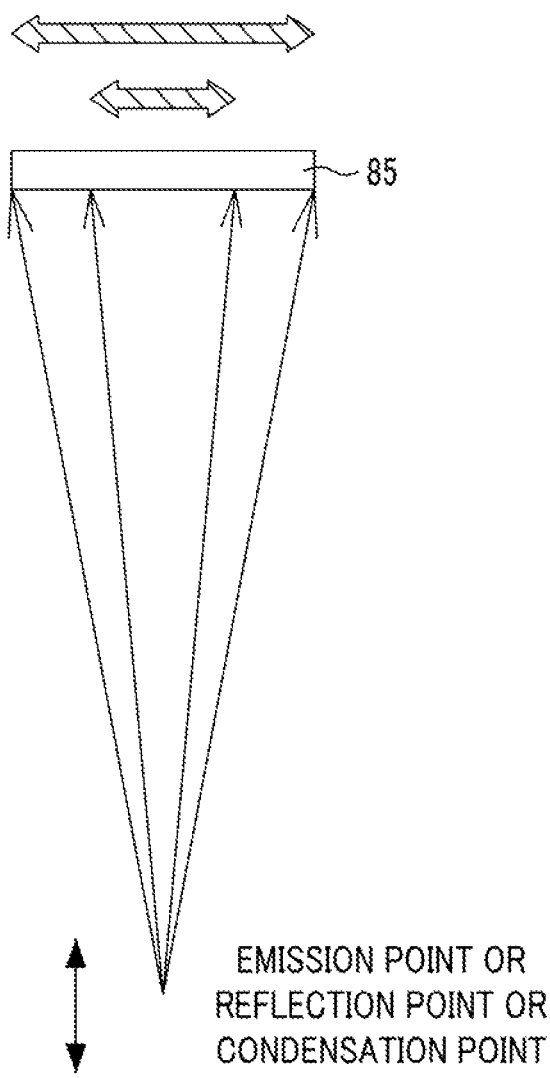
FIG. 25 is a diagram schematically illustrating a configuration in which a light-receiving region is electrically changed using an imaging device such as a CCD or a CMOS instead of a PD as a photoelectric conversion surface.

As illustrated in FIG. 25, the light-receiving region may be electrically changed (for example, pixels in a non-used range are not activated) using an imaging device such as a CCD or a CMOS instead of the PD as the photoelectric conversion surface. The light-receiving region is adjusted in this configuration. In this example, the photoelectric conversion surface of which the light-receiving region is electrically changed is referenced by reference numeral 85 for the purpose of distinction from the photoelectric conversion surface 80.

In addition to the purpose of adjusting the light-receiving area so that the center of the position variation range of the measurement target is located at the reference position, for the purpose of not changing the light-receiving area but changing the light-receiving region, the photoelectric conversion surface 80 may be constructed by an imaging device having plural light receiving elements.

Figure 26:
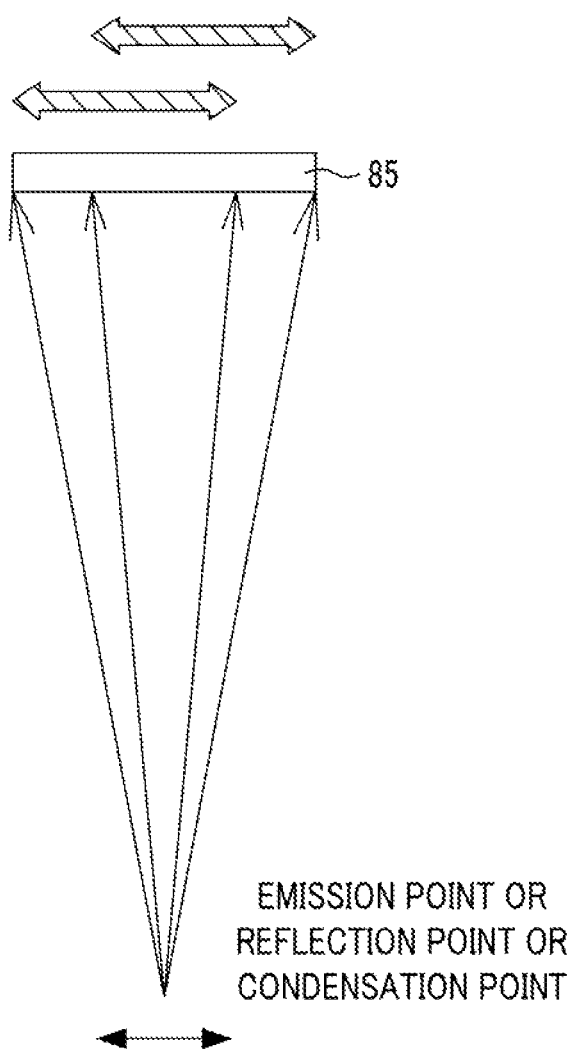
FIG. 26 is a diagram schematically illustrating a state where the light-receiving region of a photoelectric conversion surface is electrically changed for each light beam.

For example, in the third exemplary embodiment, when the positions h in the height direction of plural reflection points of the measurement object OB are measured by sequentially emitting a light beam from the light source 46 of the measuring device 10H described with reference to FIG. 17, the reflection point is shifted in the horizontal direction for each light beam. Accordingly, the light-receiving position of the photoelectric conversion surface 80 included in the photoelectric conversion unit is gradually shifted. The same is true when the positions of plural emission points are measured and when the positions of plural condensation points are measured. Therefore, as illustrated in FIG. 26, the light-receiving region may be electrically changed for each light beam (for example, pixels in a non-used range may not be activated).

The measuring device may be formed by combination of the configuration in which the light-receiving position of the photoelectric conversion surface 80 may be changed as described in Modification Example 3 and the configuration in which the light-receiving region of the photoelectric conversion surface 80 may be changed as described in Modification Example 4.

Detailed Description of Modification Examples 3 and 4

Here, an example of a produced of changing the light-receiving position or the light-receiving region in the configurations described in Modification Examples 3 and 4 will be described below in more detail.

The output ratio is calculated from the output values of two photoelectric conversion surfaces 80 measured by preliminary calibration, a displacement and a displacement direction from an optimal setting (optimal setting of at least one of the installation position and the light-receiving region of the photoelectric conversion surface 80) in which the output ratio is 1 are calculated, at least one of the installation position and the light-receiving region of at least one of the two photoelectric conversion surfaces 80 is corrected to the optimal setting, and then the measurement target is actually measured. Here, the output ratio is set to a value not including an error after the ratio of transmitted/reflected light beams of the half mirror or the sensitivity of the photoelectric conversion surface 80 is corrected. When the displacement and the displacement direction are known before measurement, the setting may be corrected to the value before measurement. The correction range may not be stepped but may include plural steps.

When a margin is present in the measuring time, plural output ratios may be calculated by performing measurement for plural settings and the result based on the setting when the output ratio is 1 may be selected and then output.

Modification Example 5

In the first to third exemplary embodiments and the above-mentioned modification examples, the respective photoelectric conversion surfaces 80 are separately configured, but the present invention is not limited to this configuration. For example, the respective photoelectric conversion surfaces 80 may be formed on the same substrate.

Figure 27:
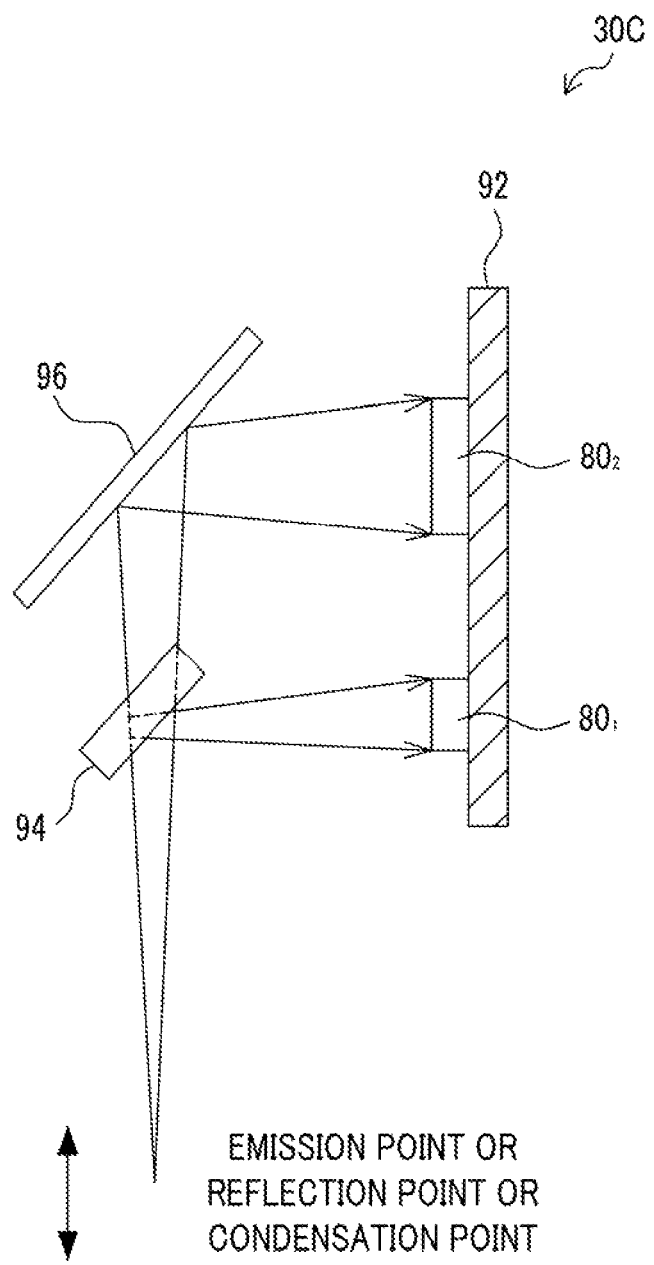
FIG. 27 is a diagram illustrating an example of a photoelectric conversion unit including plural photoelectric conversion surfaces formed on the same substrate.

FIG. 27 illustrates an example of the photoelectric conversion unit including the plural photoelectric conversion surfaces 80 formed on the same substrate. A photoelectric conversion unit 30C illustrated in FIG. 27 includes an installation substrate 92, the two photoelectric conversion surfaces $80_1$ and $80_2$, a half mirror 94, and a mirror 96.

As illustrated in FIG. 27, the two photoelectric conversion surfaces $80_1$ and $80_2$ are formed on the installation substrate 92. A light beam from a measurement target (an emission point, a reflection point, or a condensation point) is incident on the half mirror 94. The half mirror 94 transmits and reflects the incident light beam. The photoelectric conversion surface $80_1$ formed on the installation substrate 92 is disposed in the emission direction of the reflected light beam from the half mirror 94. The mirror 96 is disposed in the emission direction of the transmitted light beam from the half mirror 94, and the photoelectric conversion surface $80_2$ formed on the installation substrate 92 is disposed in the emission direction of the reflected light beam from the mirror 96. The mirror 96 reflects the light beam input from the half mirror 94 to the photoelectric conversion surface $80_2$. That is, the light beam emitted from the measurement target is incident on the photoelectric conversion surface $80_2$ via the half mirror 94 and the mirror 96.

Figure 28:
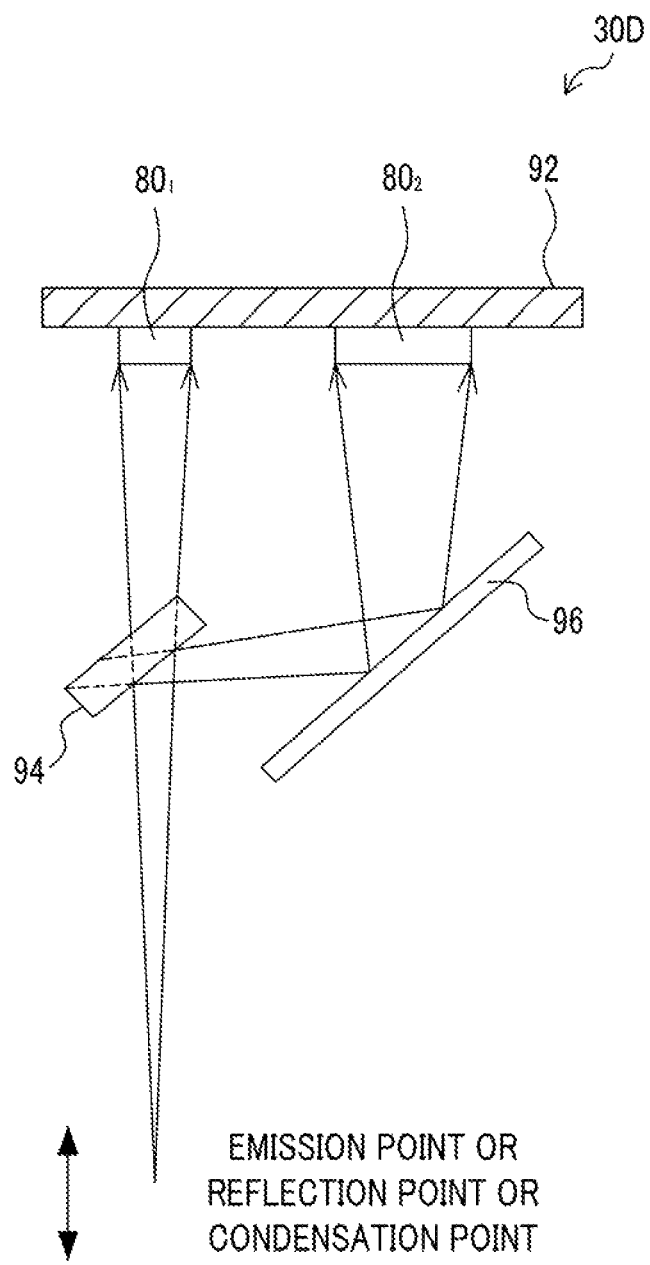
FIG. 28 is a diagram illustrating another example of a photoelectric conversion unit including plural photoelectric conversion surfaces formed on the same substrate.

FIG. 28 illustrates another example of the photoelectric conversion unit including plural photoelectric conversion surfaces 80 formed on the same substrate. A photoelectric conversion unit 30D illustrated in FIG. 28 includes the installation substrate 92, the two photoelectric conversion surfaces $80_1$ and $80_2$, the half mirror 94, and the mirror 96, similarly to the photoelectric conversion unit 30C.

As illustrated in FIG. 28, the two photoelectric conversion surfaces $80_1$ and $80_2$ are formed on the installation substrate 92. A light beam from a measurement target (an emission point, a reflection point, or a condensation point) is incident on the half mirror 94. The photoelectric conversion unit 30D is disposed so that the surface of the installation substrate 92 on which the photoelectric conversion surfaces $80_1$ and $80_2$ are formed faces the measurement target.

In the photoelectric conversion unit 30D, the photoelectric conversion surface $80_1$ formed on the installation substrate 92 is disposed in the emission direction of the transmitted light beam from the half mirror 94. The mirror 96 is disposed in the emission direction of the reflected light beam from the half mirror 94, and the photoelectric conversion surface $80_2$ formed on the installation substrate 92 is disposed in the emission direction of the reflected light beam from the mirror 96. The mirror 96 reflects the light beam input from the half mirror 94. That is, the light beam emitted from the measurement target is incident on the photoelectric conversion surface $80_1$ via the half mirror 94 and the mirror 96.

In any of the photoelectric conversion units 30C and 30D, since the light beam passing through the mirror 96 is longer in the distance (optical path length) from the measurement target than the light beams not passing through the mirror 96, it is preferable that the photoelectric conversion surface $80_2$ be treated as the photoelectric conversion surface 80 having a longer optical path length and the photoelectric conversion surface $80_1$ be treated as the photoelectric conversion surface 80 having a shorter optical path length.

In the photoelectric conversion units 30C and 30D, as described above, the photoelectric conversion surface 80 may be provided with the shielding member 70 or the lens 74. A photoelectric conversion surface including plural PDs or an imaging device such as a CCD or a CMOS may be used as the photoelectric conversion surface 80.

Modification Example 6

The number of the photoelectric conversion surfaces 80 disposed in the photoelectric conversion units 30 to 30D may be three or more. In a configuration of this case, when a measurement target (an emission point, a reflection point, or a condensation point) varies in various variation ranges, two of the plural photoelectric conversion surfaces 80 may have the relationship illustrated in FIG. 15 with the center of the variation range as the reference position.

Figure 29:
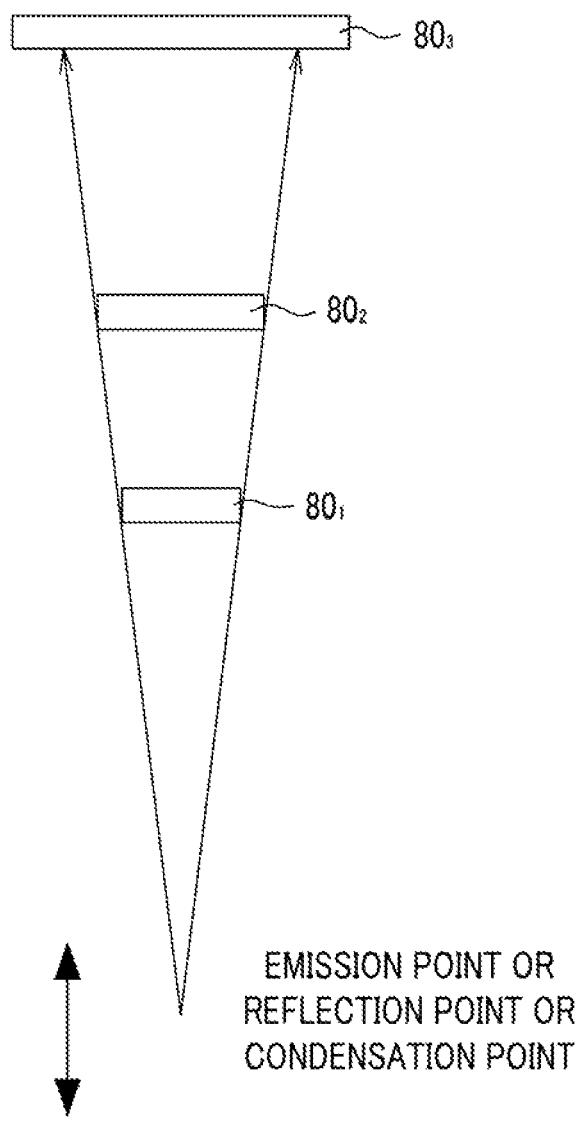
FIG. 29 is a diagram schematically illustrating an example of an arrangement state of three photoelectric conversion surfaces.
Figure 30:
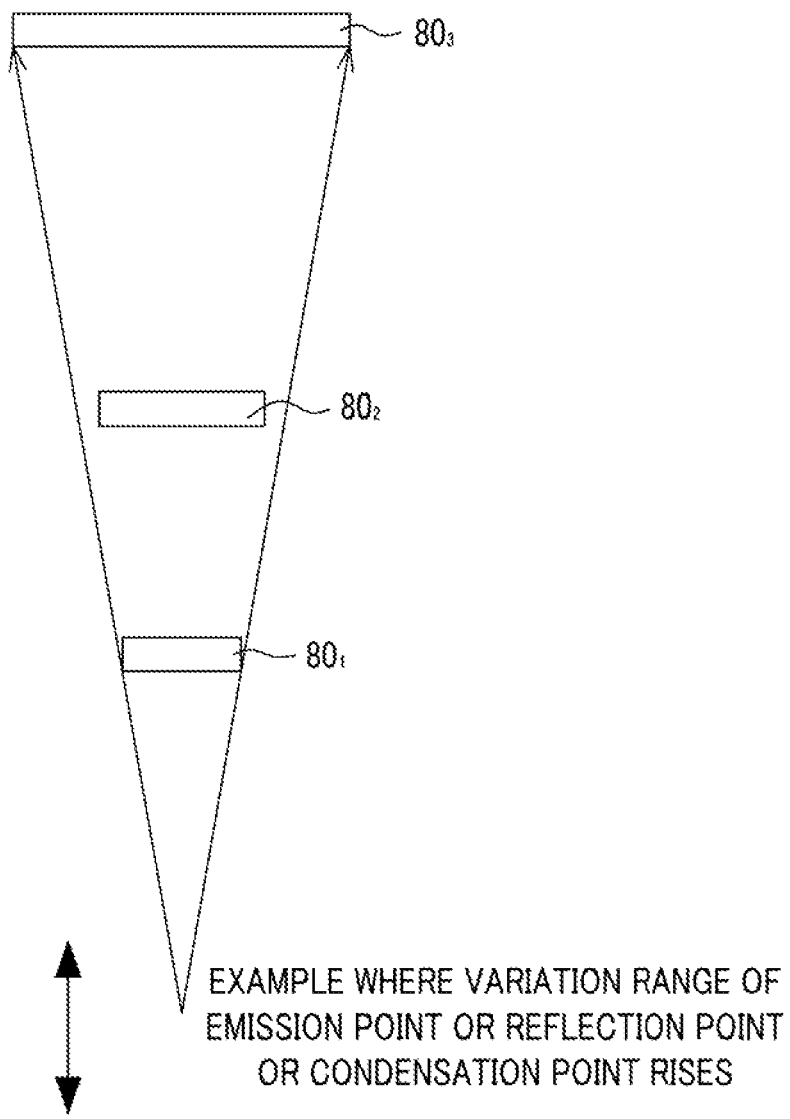
FIG. 30 is a diagram schematically illustrating an example of an arrangement state of three photoelectric conversion surfaces.

FIGS. 29 and 30 are diagrams schematically illustrating an example of the arrangement state of three photoelectric conversion surfaces $80_1$ to $80_3$. The light-receiving areas thereof are different from each other. Here, the half mirror and the reflection of a light beam from the half mirror are not illustrated, but for example, when the variation range of a measurement target is the same as illustrated in FIG. 29, the installation position of each photoelectric conversion surface 80 (or the light-receiving region of each photoelectric conversion surface 80) is adjusted so that a light beam from the measurement target passes through the outer edges of two photoelectric conversion surfaces of the three photoelectric conversion surfaces $80_1$ to $80_3$, that is, the photoelectric conversion surface $80_1$ and the photoelectric conversion surface $80_2$. When the variation range of the measurement target rises from the range illustrated in FIG. 29 and becomes the range illustrated in FIG. 30, the installation position of each photoelectric conversion surface 80 (or the light-receiving region of each photoelectric conversion surface 80) is adjusted so that the light beam from the measurement target passes through the outer edges of the photoelectric conversion surface $80_1$ and the photoelectric conversion surface $80_3$.

In this way, two photoelectric conversion surfaces of the plural photoelectric conversion surfaces 80 are adjusted so that the output ratio is 1 when the measurement target is located at the reference position. Then, the measuring unit 12 measures the position h of the measurement target as described above, using the output values of the photoelectric conversion surfaces 80 adjusted so that the output ratio is 1.

Modification Example 7

At least the photoelectric conversion surfaces 80 other than the photoelectric conversion surface 80 having the longest optical path length from the measurement target out of the plural photoelectric conversion surfaces 80 may be formed of a light-transmitting member that photo-electrically converts an incident light beam and emits (that is, transmits) the converted light beam to the side opposite to the incidence side, and the central points of the plural photoelectric conversion surfaces 90 may be arranged on a straight line so that the light-receiving surfaces of the plural photoelectric conversion surfaces 90 are parallel to or substantially parallel to each other. In this example, the photoelectric conversion surfaces are referenced by reference numeral 90 for the purpose of distinction from the photoelectric conversion surface 80 described in the above-mentioned modification examples.

Figure 31:
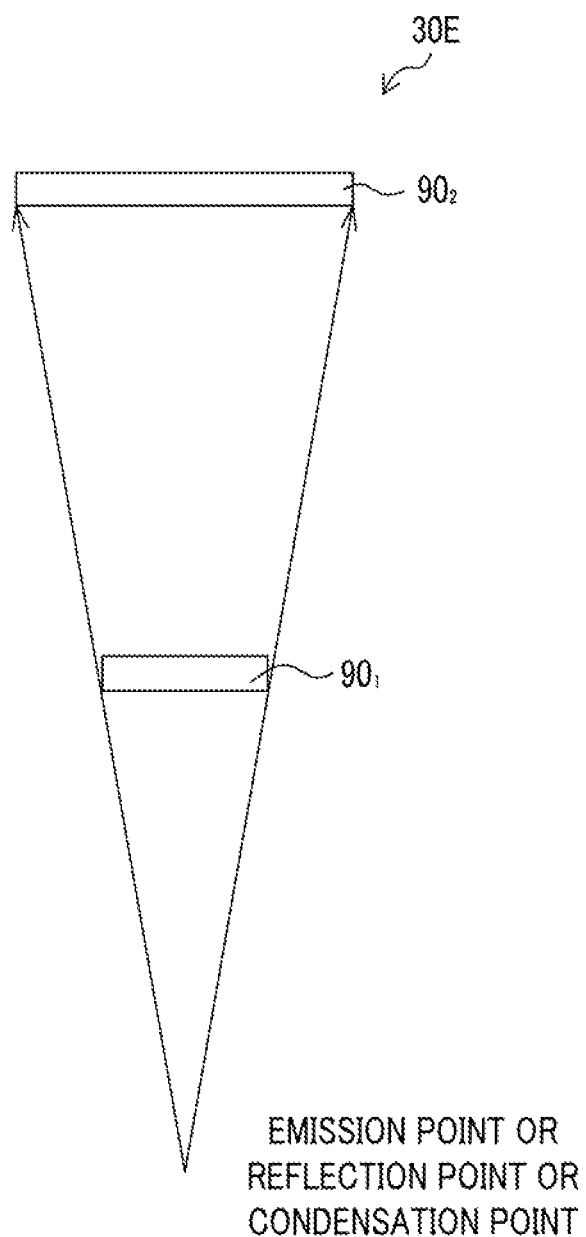
FIG. 31 is a diagram schematically illustrating a photoelectric conversion unit having two photoelectric conversion surfaces of which central points are arranged on a straight line.

FIG. 31 is a diagram schematically illustrating a photoelectric conversion unit 30E including two photoelectric conversion surfaces $90_1$ and $90_2$ arranged so that the central points are located on a straight line. At least the photoelectric conversion surface $90_1$ having a short optical path length from a measurement target is formed of a material (light-transmitting member) capable of transmitting light. The photoelectric conversion surface $90_1$ photo-electrically converts an incident light beam and emits the converted light beam to the photoelectric conversion surface $90_2$ in the subsequent stage. The photoelectric conversion surface $90_2$ in the subsequent stage may be formed of a light-transmitting member or may not be formed of a light-transmitting member.

By employing this configuration, the half mirror for separating the optical path of the two photoelectric conversion surfaces $90_1$ and $90_2$ is not necessary.

Figure 32:
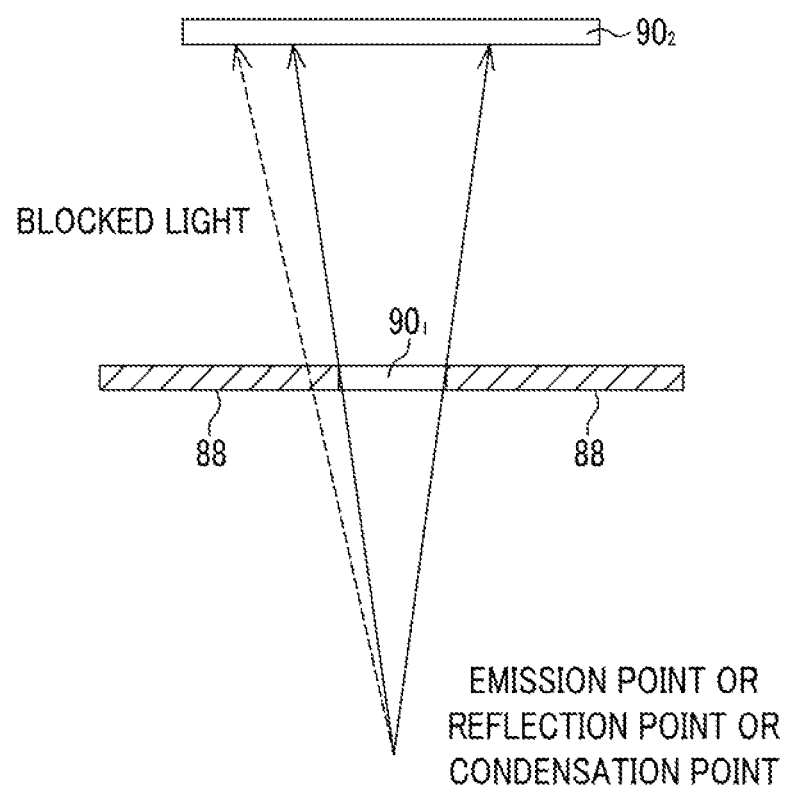
FIG. 32 is a diagram schematically illustrating a state where a light beam to reach a photoelectric conversion surface having a long optical path length is blocked by a support member supporting a photoelectric conversion surface having a short optical path length in the configuration illustrated in FIG. 31.
Figure 33:
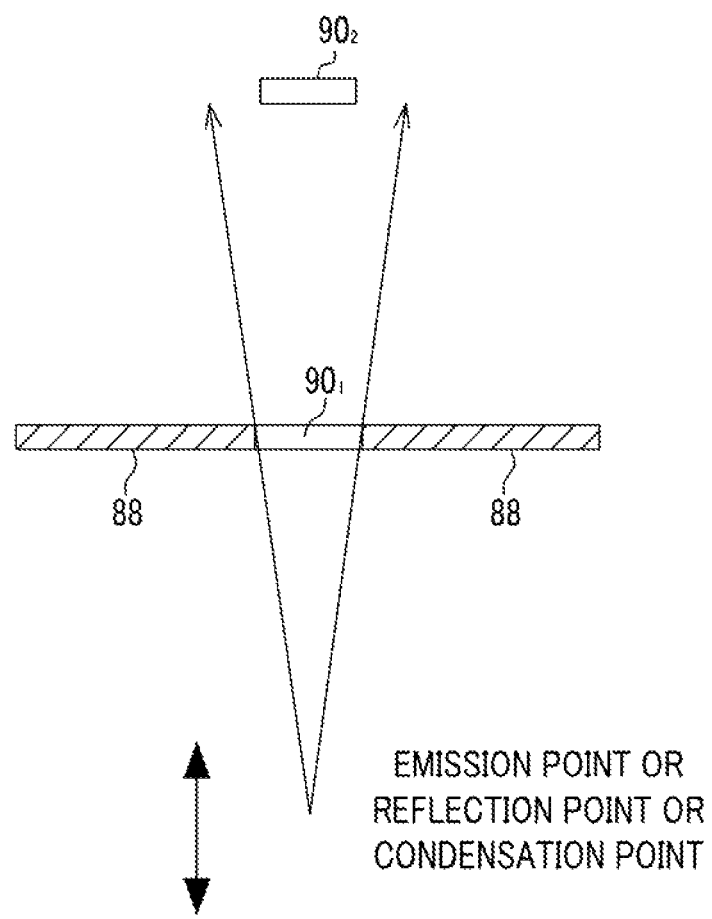
FIG. 33 is a diagram illustrating a configuration in which photoelectric conversion surfaces are designed so that a light beam passing through a photoelectric conversion surface having a short optical path length reaches a light-receiving surface of a photoelectric conversion surface having a long optical path length even when a measurement target vertically moves.

Here, when the photoelectric conversion unit has the configuration illustrated in FIG. 31, a light beam to be incident on the photoelectric conversion surface $90_2$ may be blocked by a support member 88 supporting the photoelectric conversion surface $90_1$ as illustrated in FIG. 32. Accordingly, as illustrated in FIG. 33, the positions or the sizes of the photoelectric conversion surfaces 90 need to be designed so that the light beam passing through the photoelectric conversion surface $90_1$ reaches the light-receiving surface of the photoelectric conversion surface $90_2$ even when the measurement target vertically moves. Therefore, the light-receiving area of the photoelectric conversion surface $90_2$ may be smaller than the light-receiving area of the photoelectric conversion surface $90_1$ depending on the design.

Modification Example 8

The measuring devices described in the above-mentioned exemplary embodiments and the above-mentioned modification examples are not limited to a device that measures the position h in the height direction of a measurement target. For example, the measuring devices may have a function of detecting reflectance of a measurement target in addition to the function of measuring the position h in the height direction of the measurement target. The measuring devices may additionally have a function of correcting the detected reflectance based on the measurement result of the position h in the height direction.

The above-mentioned exemplary embodiments describes the example where the measuring unit 12 is embodied by the computer 200, but the functions of detecting and correcting reflectance may be further embodied by the computer 200.

Figure 34:
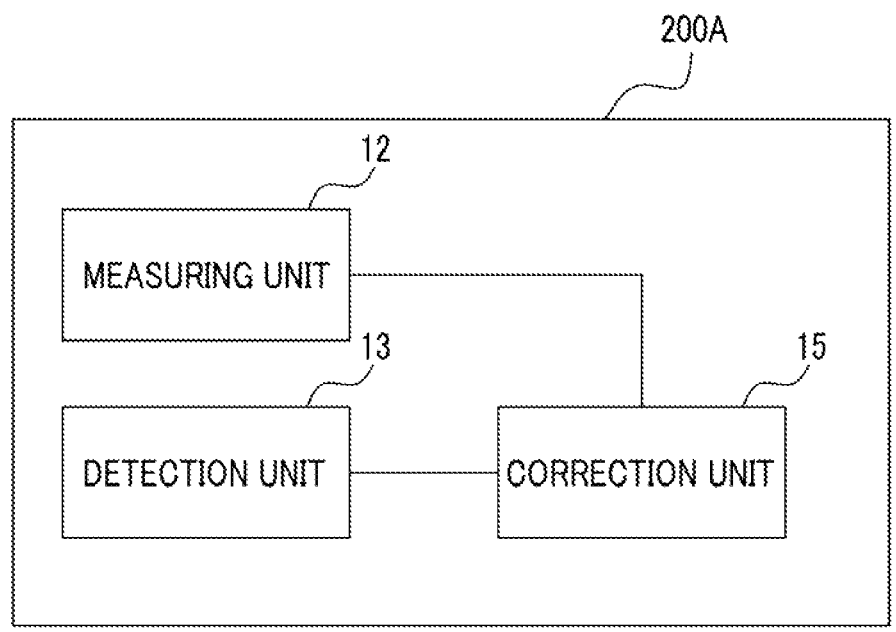
FIG. 34 is a diagram illustrating a functional configuration of a computer which serves as a detection unit detecting reflectance of a measurement target and a correction unit correcting the reflectance detected by the detection unit in addition to a measuring unit.

FIG. 34 is a diagram illustrating a functional configuration of a computer 200A which serves as a detection unit 13 detecting reflectance of a measurement target and a correction unit 15 correcting the reflectance detected by the detection unit 13 in addition to the measuring unit 12. Here, the hardware configuration of the computer 200A is the same as the computer 200 illustrated in FIG. 1, but programs stored in the ROM 16 include a program for causing the computer to serve as the detection unit 13 and a program for causing the computer to serve as the correction unit 15 in addition to a program for causing the computer 200A to serve as the measuring unit 12 and thus the programs are referenced by adding a subscript A thereto for the purpose of distinction from the computer 200.

In this modification example, the computer 200A is employed instead of the computers 200 in the measuring devices 10A to 10H. The CPU 14 executes the programs stored in the ROM 16.

Here, a method of detecting reflectance will be described in brief. First, in advance, a member with reflectance of 100% is irradiated with a light beam from the light source 40 included in the measuring devices 10A to 10H described above, the reflected light beam from the member is received by the single photoelectric conversion surface 80, and the magnitude (reference value) of the electrical signal thereof is stored. At the time of actually detecting reflectance of a measurement target, the detection unit 13 calculates a ratio of an electrical signal, which is obtained by irradiating the measurement target with a light beam from the light source 40 and photoelectrically converting the reflected light beam, to the reference value stored in advance and detects the calculated value as the reflectance.

In general, when the position h in the height direction from a measurement object to the photoelectric conversion surface 80 varies, the reflectance also varies. Accordingly, the correction unit 15 corrects the reflectance using the measured value of the position h in the height direction of the measurement target which is measured by the measuring unit 12. The relationship between the position h and a correction value may be calculated and stored by experiments or the like in advance. The correction unit 15 corrects the reflectance detected by the detection unit 13 using the correction value stored in advance in correlation with the position h. For example, the correction unit 15 performs the correction operation using a predetermined calculation method such as multiplying the correction value by the reflectance detected by the detection unit 13 or subtracting the correction value therefrom. Accordingly, it is possible to obtain more accurate reflectance.

Modification Example 9

The photoelectric conversion surfaces 80 and 90 receive a light beam, photo-electrically convert the received light beam, and output an electrical signal. At this time, ambient light may be incident on the photoelectric conversion surfaces 80 and 90. Therefore, in order to remove the ambient light, the output values of the photoelectric conversion surfaces 80 and 90 when the emission point P or the light source 40 are turned off are measured in advance and are stored as reference values in a storage medium such as the ROM 16. A value obtained by subtracting the reference values from the output values of the photoelectric conversion surfaces 80 and 90 when the emission point P or the light source 40 is turned off (when light is applied as a measurement target) may be calculated and then the output ratio of the two photoelectric conversion surfaces 80 and 90 may be calculated.

Modification Example 10

The light beam received by the photoelectric conversion surfaces 80 and 90 is not limited to an emitted light beam or a reflected light beam. For example, a transmitted light beam passing through the measurement object OB may be received and photo-electrically converted.

In this case, in the photoelectric conversion surfaces 80 and 90, the photoelectric conversion unit (including the photoelectric conversion surfaces, the half mirror, and the like as in the photoelectric conversion units 30A to 30E) is disposed on the side transmitting the light beam applied to the measurement object OB, that is, the side opposite to the light source 40.

Modification Example 11

The first to third exemplary embodiments and the modification examples describe above the examples where the photoelectric conversion unit includes plural photoelectric conversion surfaces, but the number of photoelectric conversion surfaces may be one. Here, when the number of photoelectric conversion surfaces is one, a single photoelectric conversion surface may be provided with a moving mechanism so as to be movable, the single photoelectric conversion surface may be moved to change the optical path length by the moving mechanism, the output value from the photoelectric conversion surface may be acquired for each optical path length, the output ratio may be calculated using two output values, and the position h of a measurement target may be measured as described above. By employing this configuration, it is possible to simply measure the position h of a measurement target even when the number of photoelectric conversion surfaces is one. The measurement may be performed at a higher speed with a configuration in which the measurement is performed using plural photoelectric conversion surfaces without moving the photoelectric conversion surface, but this modification example is useful when the number of photoelectric conversion surfaces is limited in view of cost.

While various measuring devices are exemplified hitherto, the measuring device is not limited to the above-mentioned exemplary embodiments and the present invention may be modified, changed, or improved in various forms. For example, the above-mentioned exemplary embodiments or modification examples may be appropriately combined.

The foregoing description of the exemplary embodiments of the present invention has been provided for the purposes of illustration and description. It is not intended to be exhaustive or to limit the invention to the precise forms disclosed. Obviously, many modifications and variations will be apparent to practitioners skilled in the art. The embodiments were chosen and described in order to best explain the principles of the invention and its practical applications, thereby enabling others skilled in the art to understand the invention for various embodiments and with the various modifications as are suited to the particular use contemplated. It is intended that the scope of the invention be defined by the following claims and their equivalents.

What is claimed is:

1. A measuring device comprising:
   a photoelectric conversion unit that receives a light beam emitted or reflected from a position measurement object by different optical path lengths and that outputs an electrical signal corresponding to intensity of the received light beam for each optical path length; and
   a measuring unit that measures a position of the position measurement object based on a ratio of two electrical signals out of the electrical signals by optical path lengths acquired from the photoelectric conversion unit,
   wherein a condenser lens is not disposed between the photoelectric conversion unit and the position measurement object so that the photoelectric conversion unit only receives a diffused light beam having a spread angle.

2. The measuring device according to claim 1, wherein the photoelectric conversion unit includes a plurality of photoelectric conversion surfaces having different optical path lengths, and outputs the electrical signal corresponding to the intensity of the received light beam for each optical path length by receiving the light beam emitted or reflected from the position measurement object through the plurality of photoelectric conversion surfaces.

3. The measuring device according to claim 1, further comprising:
   a light source that sequentially emits a plurality of light beams incident on the position measurement object and having different optical axis positions, the plurality of light beams having substantially equal irradiation angles,
   wherein the measuring unit acquires the two electrical signals for each of the plurality of light beams sequentially emitted from the light source, calculates the ratio thereof, and measures positions of a plurality of points of the position measurement object based on the ratio for each of the plurality of light beams.

4. The measuring device according to claim 2, wherein the plurality of photoelectric conversion surfaces includes a first photoelectric conversion surface and a second photoelectric conversion surface, the first photoelectric conversion surface having a shorter optical path length than an optical path length of the second photoelectric conversion surface and being a smaller size than a size of the second photoelectric conversion surface.

5. The measuring device according to claim 2, wherein at least one of the optical path lengths from a predetermined reference position and a light-receiving area in the two photoelectric conversion surfaces is adjusted in advance so that a ratio of the electrical signals output from the two photoelectric conversion surfaces out of the plurality of photoelectric conversion surfaces is 1 or is in a predetermined range including 1 in a state where the position measurement object is disposed at the reference position, and
wherein the measuring unit measures a position of the position measurement object based on the ratio of the electrical signals output from the two photoelectric conversion surfaces adjusted so that the ratio is 1 or is in a predetermined range including 1.

6. The measuring device according to claim 3, wherein the light source includes a light emitting diode (LED) array or a vertical cavity surface emitting laser (VCSEL) array, and
the LED array or the VCSEL array sequentially emits the plurality of light beams.

7. The measuring device according to claim 1, wherein the photoelectric conversion unit is configured so that a difference in the optical path length from a reference position where the position measurement object to be positioned to the two photoelectric conversion surfaces is equal to or greater than 5% of a smaller optical path length in a state where the position measurement object is disposed at the predetermined reference position.

8. The measuring device according to claim 5, wherein the measuring unit, in a state where the position measurement object is disposed so that an irradiation position of the position measurement object irradiated with any one light beam of a plurality of light beams is the reference position, acquires the electrical signals output from the two photoelectric conversion surfaces for each of the plurality of light beams sequentially emitted from the light source, calculates the ratio, and measures the positions of a plurality of points of the position measurement object based on the ratio for each of the plurality of light beams.

9. The measuring device according to claim 2, wherein the light-receiving area of at least one of the plurality of photoelectric conversion surfaces is variable.

10. The measuring device according to claim 2, wherein at least one of the plurality of photoelectric conversion surfaces is provided with a moving mechanism that moves a position of the corresponding photoelectric conversion surface to adjust a distance from the corresponding photoelectric conversion surface to the position measurement object.

11. The measuring device according to claim 2, wherein at least the photoelectric conversion surfaces other than the photoelectric conversion surface having the longest optical path length from the position measurement object out of the plurality of photoelectric conversion surfaces is formed of a light-transmitting member that photo-electrically converts an incident light beam and that emits the converted light beam to a side opposite to the incidence side, and the plurality of photoelectric conversion surfaces are arranged so that central points thereof are located on a straight line.

12. The measuring device according to claim 1, wherein the photoelectric conversion unit receives a reflected light beam from the position measurement object and outputs an electrical signal corresponding to the intensity of the received light beam by optical path lengths, and wherein the measuring device further comprises:

a detection unit that detects reflectance of the position measurement object using one electrical signal out of the electrical signals by the optical path lengths acquired by the photoelectric conversion unit; and a correction unit that corrects the detected reflectance using the measurement result of the measuring unit.

13. The measuring device according to claim 1, wherein the photoelectric conversion unit is configured so that a difference in the optical path length from a reference position where the position measurement object to be positioned to the two photoelectric conversion surfaces is equal to or greater than 5% of a smaller optical path length in a state where the position measurement object is disposed at the predetermined reference position.

* * * * *